United States Patent
Badawi et al.

(10) Patent No.: US 11,925,657 B2
(45) Date of Patent: *Mar. 12, 2024

(54) FORMULATIONS AND METHODS FOR TREATING CONDITIONS OF THE EYE

(71) Applicant: Sight Sciences, Inc., Menlo Park, CA (US)

(72) Inventors: Paul Badawi, Atherton, CA (US); David Y. Badawi, Glenview, IL (US)

(73) Assignee: SIGHT SCIENCES, INC., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/088,347

(22) Filed: Dec. 23, 2022

(65) Prior Publication Data

US 2023/0210878 A1 Jul. 6, 2023

Related U.S. Application Data

(63) Continuation of application No. 17/868,696, filed on Jul. 19, 2022, now Pat. No. 11,554,134, which is a continuation of application No. 17/534,349, filed on Nov. 23, 2021, now Pat. No. 11,419,886.

(60) Provisional application No. 63/254,958, filed on Oct. 12, 2021, provisional application No. 63/117,393, filed on Nov. 23, 2020.

(51) Int. Cl.
| | |
|---|---|
| *A61K 31/7052* | (2006.01) |
| *A61K 9/00* | (2006.01) |
| *A61K 31/194* | (2006.01) |
| *A61K 31/7048* | (2006.01) |
| *A61K 47/10* | (2017.01) |
| *A61P 27/02* | (2006.01) |
| *A61P 27/04* | (2006.01) |

(52) U.S. Cl.
CPC ........ *A61K 31/7052* (2013.01); *A61K 9/0019* (2013.01); *A61K 9/0048* (2013.01); *A61K 31/194* (2013.01); *A61K 31/7048* (2013.01); *A61K 47/10* (2013.01); *A61P 27/02* (2018.01); *A61P 27/04* (2018.01)

(58) Field of Classification Search
None
See application file for complete search history.

(56) References Cited

U.S. PATENT DOCUMENTS

| | | |
|---|---|---|
| 4,957,918 A | 9/1990 | Martin et al. |
| 5,434,187 A | 7/1995 | Egerer et al. |
| 5,614,545 A | 3/1997 | Martin et al. |
| 6,107,289 A | 8/2000 | Sullivan |
| 7,659,259 B2 | 2/2010 | Xia et al. |
| 7,732,415 B2 | 6/2010 | Dawson et al. |
| 8,148,389 B2 | 4/2012 | Nakamura et al. |
| 8,349,806 B2 | 1/2013 | Brubaker et al. |
| 8,900,626 B2 | 12/2014 | Ogawa et al. |
| 8,987,218 B2 | 3/2015 | Kaoukhov et al. |
| 9,034,830 B2 | 5/2015 | Nanduri et al. |
| 9,044,508 B2 | 6/2015 | Bowman et al. |
| 9,096,538 B2 | 8/2015 | Nakamura et al. |
| 9,439,917 B1 | 9/2016 | Shah et al. |
| 9,539,204 B2 | 1/2017 | Kido et al. |
| 9,999,594 B2 | 6/2018 | Kido et al. |
| 10,058,615 B2 | 8/2018 | Günther et al. |
| 10,744,147 B2 | 8/2020 | Mallard |
| 11,419,886 B2 | 8/2022 | Badawi et al. |
| 11,457,626 B2 | 10/2022 | Dyer |
| 11,554,134 B2 | 1/2023 | Badawi et al. |
| 2004/0198763 A1 | 10/2004 | Ueno |
| 2005/0043286 A1 | 2/2005 | Fsadni et al. |
| 2006/0036220 A1 | 2/2006 | Kawahara et al. |
| 2007/0004672 A1 | 1/2007 | Jani et al. |
| 2008/0057022 A1 | 3/2008 | Xia |
| 2008/0076793 A1 | 3/2008 | Fsadni et al. |
| 2008/0275000 A1 | 11/2008 | Xia et al. |
| 2008/0280853 A1 | 11/2008 | Xia et al. |
| 2008/0312194 A1 | 12/2008 | Ousler, III et al. |
| 2009/0093421 A1 | 4/2009 | Kaoukhov et al. |
| 2009/0318422 A1 | 12/2009 | Isowaki et al. |
| 2010/0022465 A1 | 1/2010 | Brubaker et al. |
| 2010/0150992 A1 | 6/2010 | Kawahara et al. |
| 2010/0160293 A1 | 6/2010 | Tojo et al. |
| 2010/0190734 A1 | 7/2010 | Brazzell et al. |
| 2011/0059925 A1 | 3/2011 | Donnenfeld |
| 2011/0104083 A1 | 5/2011 | Nanduri et al. |
| 2011/0158983 A1 | 6/2011 | Bascomb et al. |
| 2011/0294897 A1 | 12/2011 | Aberg et al. |
| 2013/0045927 A1 | 2/2013 | Dana et al. |
| 2013/0144128 A1 | 6/2013 | De Juan, Jr. et al. |

(Continued)

FOREIGN PATENT DOCUMENTS

| | | |
|---|---|---|
| WO | WO-2006/087968 A1 | 8/2006 |
| WO | WO-2009/120881 A1 | 10/2009 |

(Continued)

OTHER PUBLICATIONS

AzaSite® (2017). Highlights of Prescribing Information, 3 total pages.
Azyter® (2019). Summary of Product Characteristics, 7 total pages.
Chhadva, P. et al. (2017). "Meibomian Gland Disease: The Role of Gland Dysfunction in Dry Eye Disease," Ophthalmology 124(11 Suppl):S20-S26. S20-S26.
fda.gov (2014). Center for Drug Evaluation and Research, Application No. 206255Orig1s000, Medical Review(s), NDA 206255, 151 total pages.
Foulks, G.N. et al. (2010). "Topical azithromycin therapy for meibomian gland dysfunction: clinical (response and lipid alterations," Cornea 29:781-788.

(Continued)

*Primary Examiner* — Dale R Miller
(74) *Attorney, Agent, or Firm* — Cooley LLP

(57) ABSTRACT

The present disclosure relates to methods of treating chronic conditions of the eye, such as dry eye disease and blepharitis, as well as to methods for increasing secretion of meibum. This disclosure also relates to formulations suitable for treating chronic conditions of the eye such as dry eye disease and blepharitis.

27 Claims, No Drawings

(56) References Cited

U.S. PATENT DOCUMENTS

| | | |
|---|---|---|
| 2013/0190317 A1 | 7/2013 | Chappuis et al. |
| 2013/0281390 A1 | 10/2013 | Brubaker |
| 2014/0142055 A1 | 5/2014 | Hosseini et al. |
| 2014/0274924 A1 | 9/2014 | Bowman et al. |
| 2015/0174211 A1 | 6/2015 | Nanduri et al. |
| 2015/0224064 A1 | 8/2015 | Günther et al. |
| 2016/0243116 A1 | 8/2016 | Jain et al. |
| 2017/0087179 A1 | 3/2017 | Amselem et al. |
| 2018/0071229 A1 | 3/2018 | Günther et al. |
| 2019/0000871 A1 | 1/2019 | Jain et al. |
| 2020/0061002 A1 | 2/2020 | Horn |
| 2020/0297820 A1 | 9/2020 | Sullivan et al. |
| 2020/0338105 A1 | 10/2020 | Tan et al. |
| 2021/0052490 A1 | 2/2021 | Padmanabhan |
| 2021/0052493 A1 | 2/2021 | Sinclair |
| 2022/0160668 A1 | 5/2022 | Badawi et al. |
| 2022/0233506 A1 | 7/2022 | Liu et al. |

FOREIGN PATENT DOCUMENTS

| | | |
|---|---|---|
| WO | WO-2010/092312 A1 | 8/2010 |
| WO | WO-2011/053792 A4 | 5/2011 |
| WO | WO-2011/053801 A4 | 5/2011 |
| WO | WO-2012/092375 A1 | 7/2012 |
| WO | WO-2016/022066 A1 | 2/2016 |
| WO | WO-2017/011071 A1 | 1/2017 |
| WO | WO-2017/055295 A1 | 4/2017 |
| WO | WO-2017/089980 A1 | 6/2017 |
| WO | WO-2017/103583 A1 | 6/2017 |
| WO | WO-2018/203040 A1 | 11/2018 |
| WO | WO-2019/104207 A2 | 5/2019 |
| WO | WO-2019/104207 A3 | 5/2019 |
| WO | WO-2019/113475 A1 | 6/2019 |
| WO | WO-2020/077284 A1 | 4/2020 |
| WO | WO-2021/033154 A1 | 2/2021 |
| WO | WO-2021/067823 A9 | 4/2021 |
| WO | WO-2021/087051 A1 | 5/2021 |

OTHER PUBLICATIONS

International Search Report dated Mar. 18, 2022, for PCT Application No. PCT/US2021/060653, filed on Nov. 23, 2021, 4 pages.

Klarity-A™ (2019). Product Insert and Information, 2 total pages.

Lemp, M.A. et al. (2012). "Distribution of aqueous-deficient and evaporative dry eye in a clinic-based patient cohort: a retrospective study," Cornea 31:472-478.

Nelson, J.D. et al. (2017). "TFOS DEWS II Introduction," Ocul. Surf. 15:269-275.

Non-Final Office Action dated Jan. 31, 2022, for U.S. Appl. No. 17/534,349, filed Nov. 23, 2021, 11 pages.

Notice of Allowance dated May 24, 2022, for U.S. Appl. No. 17/534,349, filed Nov. 23, 2021, 11 pages.

Notice of Allowance dated Sep. 26, 2022, for U.S. Appl. No. 17/868,696, filed Jul. 19, 2022, 5 pages.

Schaller, M. et al. (2016). "Rosacea management: update on general measures and topical treatment options," JDDG: Journal der Deutschen Dermatologischen Gesellschaft 14:17-27.

Soolantra® (2014). Highlights of Prescribing Information, 8 total pages.

Written Opinion of the International Searching Authority dated Mar. 18, 2022, for PCT Application No. PCT/US2021/060653, filed on Nov. 23, 2021, 9 pages.

FORMULATIONS AND METHODS FOR TREATING CONDITIONS OF THE EYE

CROSS-REFERENCE TO RELATED APPLICATIONS

This application is a continuation of U.S. application Ser. No. 17/868,696, filed on Jul. 19, 2022, which is a continuation of U.S. application Ser. No. 17/534,349, filed on Nov. 23, 2021, now U.S. Pat. No. 11,419,886, which claims the benefit of U.S. Provisional Application No. 63/117,393, filed Nov. 23, 2020, and U.S. Provisional Application No. 63/254,958 filed Oct. 12, 2021, the disclosure of each of which is hereby incorporated by reference in its entirety.

TECHNICAL FIELD

This disclosure relates generally to treating diseases or conditions of the eye.

BACKGROUND

Dry eye disease (DED) encompasses a number of disease states, defined by the TFOS DEWS II (*Ocul. Surf,* 2017, 15(3), 269-650) as "a multifactorial disease of the ocular surface characterized by a loss of homeostasis of the tear film, and accompanied by ocular symptoms, in which tear film instability and hyperosmolarity, ocular surface inflammation and damage, and neurosensory abnormalities play etiological roles." DED can be generally divided into two classes: aqueous tear-deficient dry eye (ADDE) and evaporative dry eye (EDE), each of which can be divided further into subclasses. One of the leading conditions associated with DED, and in particular EDE, is meibomian gland dysfunction (MGD), which is itself an umbrella term encompassing several disorders, wherein disruption and obstruction of the meibomian gland negatively impacts the quality and quantity of meibum, a lipid-rich secretion that protects the ocular surface from damage and premature evaporation of tears (Chhadva, et al., *Ophthalmology,* 2017, 124 (11 Suppl), S20-S26). There are approximately 20-40 meibomian glands in each eyelid and they are responsible for producing meibum that coats the tears and prevents premature tear evaporation. When the meibomian glands are healthy, patent, and functioning properly, meibum assumes a liquid, olive-oil like consistency. Every blink applies an expression force to the meibomian glands and some clear liquid meibum is expressed from the gland orifice and fortifies the tear's outermost lipid layer. With MGD-based EDE, the development of an imbalance in natural lipids and lipid chemistry results in a higher meibum melting temperature, which ultimately leads to meibum transitioning from a healthy, clear, liquid state to a cloudy, semi-hardened state to an advanced, diseased, hardened state. Eventually as the disease progresses and the lipid chemistry of meibum worsens, the hardened meibum becomes unavailable and inexpressible resulting in a low quality tear lipid layer and premature tear evaporation. In obstructive MGD, the blink results in little to no expression of meibum due to its hardened physiochemical state and inexpressibility, a compromised lipid layer, and accelerated tear evaporation.

Globally, the prevalence of dry eye disease (DED) is estimated to be between 5 to 20 percent, and approximately 16 million Americans have been diagnosed. It is estimated that 86% of these DED sufferers have MGD-associated EDE (Letup, et al., *Cornea,* 2012, 472-478). Those with DED suffer from either inadequate tear production, poor quality of tears, or both, which results in redness, stinging, burning, itching, light sensitivity, watery eyes, blurry vision, irregularities of the ocular surface, and damage to corneal or conjunctival epithelium and tissues. It is believed that a majority of dry eye patients have at least some degree of both aqueous deficiency and lipid deficiency. Treatment is largely palliative, and no broad cure for DED has been developed.

Relatedly, blepharitis, which could be associated with MGD, is an inflammatory condition of the eyelids, that can cause irritation, reddening, itching, burning, edema, and crusting, among other symptoms. Blepharitis can lead to permanent alterations of the eyelid margin. The condition is generally into two categories based on location. Anterior blepharitis occurs on the outer edges of the eyelids and is typically associated with bacterial infection. Posterior blepharitis, which occurs on the inner edges of the eyelids, can result when the meibomian glands produce reduced or poor quality meibum, resulting in excessive evaporation of water from the ocular surface.

There are currently no FDA approved treatments for blepharitis, and there are only four FDA approved drugs (Restasis®, Xiidra®, Cequa®, and Eysuvis®) for treating dry eye, which all act to reduce inflammatory aspects of the condition. In cases where bacterial infection results, topical or oral antibiotics may be administered, although these might not treat the underlying cause of the disease, and chronic use can result in undesired toxicity or side effects. Available treatment strategies are therefore largely palliative, and focus on maintaining proper lid hygiene. Eyelid warming using warm compresses is the standard eyelid therapy to increase meibum fluidity in patients with obstructed meibomian glands, but warm compresses are inexact and often ineffective (i.e., are too hot, are not hot enough for long enough, cool off too fast to do so effectively, do not conform to the eyelids sufficiently enough to achieve requisite sufficiently elevated meibum melting temperatures), compliance is an issue, and chronic use can result in thermal injury to ocular tissue. Opening of obstructed meibomian glands by physical expression or lid massage can improve secretion and dry eye symptoms, but compliance remains an issue as with warm compresses, the necessary procedures can cause damage to sensitive tissues (e.g., undesirable corneal remodeling from rubbing the eyelids and applying undesirable pressure on the cornea), and the therapeutic effects are short-lived.

Accordingly, there is a need for effective, long-term methods of treating disorders of the eye, including DED and blepharitis, particularly when the disorder is due to obstructed meibomian glands due to hardened meibum, and when the disorder persists chronically, over months, years, or an entire lifetime.

SUMMARY

Formulations and methods for treating dry eye disease are disclosed herein. In some embodiments, the method for treating dry eye disease in a subject in need thereof may include administering to the subject a pharmaceutical formulation comprising a sub-antibiotic dose of azithromycin. The method may include administering a pharmaceutical formulation to the eyelid. The method may also include administering the pharmaceutical formulation daily for at least 1 month.

In some embodiments, a method for treating blepharitis in a subject in need thereof is disclosed and may include administering to the subject a pharmaceutical formulation comprising a sub-antibiotic dose of azithromycin. The method may include administering a pharmaceutical formulation to the eyelid. The method may also include administering the pharmaceutical formulation daily for at least 1 month.

In other embodiments, a method for increasing secretion of meibum in a subject in need thereof is disclosed and may include administering to the subject a pharmaceutical formulation comprising a sub-antibiotic dose of azithromycin. The method may include administering a pharmaceutical formulation to the eyelid. The method may also include administering the pharmaceutical formulation daily for at least 1 month.

In some embodiments, a method for treating dry eye disease in a subject in need thereof comprises administering to the subject a pharmaceutical formulation comprising a sub-antiparasitic dose of an avermectin. The method may include administering a pharmaceutical formulation to the eyelid. The method may also include administering the pharmaceutical formulation daily for at least 1 month.

In some embodiments a method for treating blepharitis in a subject in need thereof may include administering to the subject a pharmaceutical formulation comprising a sub-antiparasitic dose of an avermectin. The method may include administering a pharmaceutical formulation to the eyelid. The method may also include administering the pharmaceutical formulation daily for at least 1 month.

In other embodiments, a method for increasing secretion of meibum in a subject in need thereof may include administering to the subject a pharmaceutical formulation comprising a sub-antiparasitic dose of an avermectin. The method may include administering a pharmaceutical formulation to the eyelid. The method may also include administering the pharmaceutical formulation daily for at least 1 month.

In other embodiments, a method for treating dry eye disease or blepharitis in a subject in need thereof may include administering to the subject a pharmaceutical formulation of azelaic acid. The method may include administering a pharmaceutical formulation to the eyelid. The administration of such a pharmaceutical formulation may reduce a symptom of dry eye disease or blepharitis. The method may also include administering the pharmaceutical formulation daily for at least 1 month.

In other embodiments, a method for increasing secretion of meibum in a subject may include administering a pharmaceutical formulation of azelaic acid. The method may include administering a pharmaceutical formulation to the eyelid. The administration of such a pharmaceutical formulation may reduce a symptom of inadequate tear production or poor quality of tears.

In other embodiments, a method for treating dry eye disease, treating blepharitis, or increasing secretion of meibum in a subject in need thereof in a subject in need thereof may include administering to the eyelid of the subject a pharmaceutical formulation. The pharmaceutical formulation may include between about 1% and about 20% azelaic acid. The pharmaceutical formulation may include between about 0.1% to about 0.5% azithromycin. The method may further include administering the pharmaceutical formulation daily for at least a month.

Pharmaceutical formulations are also disclosed herein. In some embodiments, a pharmaceutical formulation for treating a condition of the eye may include a sub-antibiotic dose of azithromycin. A pharmaceutical formulation for treating a treating a condition of the eye may include a sub-antiparasitic dose of an avermectin.

In other embodiments, a pharmaceutical formulation for treating a condition of the eye may include a sub-antibiotic dose of azithromycin and a sub-antiparasitic dose of an avermectin. A pharmaceutical formulation for treating a condition of the eye may include a sub-antibiotic dose of azithromycin and a sub-antiparasitic dose of an avermectin and may further include an immunosuppressant.

In other embodiments, a pharmaceutical formulation for treating a condition of the eye may include a sub-antibiotic dose of azithromycin or a sub-antiparasitic dose of an avermectin, and azelaic acid.

DETAILED DESCRIPTION

The following description, for purposes of explanation, uses specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and embodiments are possible in view of the teachings disclosed herein.

Described herein are embodiments of pharmaceutical formulations and methods for treating conditions of the eye. For example, pharmaceutical formulations and methods such as those described herein may be used to treat dry eye disease (DED). In some embodiments, such formulations and methods may be used to treat blepharitis. In some embodiments, the blepharitis is caused by demodex, while in other embodiments, the blepharitis is not caused by demodex. As another example, in some embodiments, such formulations and methods may be used to increase or enhance secretion of meibum. In some embodiments, such formulations and methods may be used to increase secretion or enhance the quality of meibum.

As used herein, "treat" or "treating" a disease or condition may mean to reduce, alleviate, and/or eliminate one or more symptoms of the disease or condition. For instance, a method of treating dry eye disease disclosed herein may result in the reduction of one or more symptoms of dry eye disease.

There are currently few effective, long-term formulations or methods of treatment for conditions of the eye, such as dry eye disease and blepharitis. Commercially approved treatments are limited and target specific symptoms or causes, such as inflammation or bacterial infection. In contrast, the formulations and methods described herein provide several advantages, including the ability to dose long term and to generally improve meibum quality and increase secretion in those individuals who would benefit therefrom. Additional beneficial features are described in more detail below.

Pharmaceutical Formulations

Generally, in some embodiments, a pharmaceutical formulation for treating a condition of the eye may include an antibiotic, an antiparasitic, and/or a dicarboxylic acid (e.g., azelaic acid). For instance, the antibiotic may be azithromycin. In particular, these formulations may include a sub-antibiotic dose of an antibiotic such as azithromycin. "Sub-antibiotic", as used herein, refers to an amount or concentration of antibiotic agent that is below what is typically administered to kill or inhibit the growth of bacteria, or an amount or concentration of antibiotic agent that is below what is clinically useful for killing or inhibiting growth of bacteria. For instance, a sub-antibiotic amount of azithromycin may be below 1%. For sake of clarity, percent of a component of a formulation described herein can mean w/v, w/w, or v/v percent. For example, "below 1%" can be read to mean below 1% weight/volume (% w/v), below 1% weight/weight (% w/w), or below 1% volume/volume (% v/v). In some embodiments, a pharmaceutical formulation for treating a condition of the eye may include brimonidine, oxymetazoline, or metronidazole.

Notably, the sub-antibiotic formulations disclosed herein are contrasted with commercial formulations of antibiotics that are used in ophthalmic applications. For instance, AzaSite® and Klarity-A™ contain 1% azithromycin and are used to treat bacterial conjunctivitis, or infections of the eye. Azyter® is another commercial ophthalmic formulation containing 1.5% azithromycin. However, formulations such as Azasite®, Klarity-A™, and Azyter® are not suitable chronic use. The AzaSite label states that "prolonged use may result in overgrowth of non-susceptible organisms, including fungi," potentially leading to new and more difficult-to-treat infections. Further, U.S. Pat. No. 8,349,806 discloses an anti-inflammatory mechanism of action for AzaSite, however, in 2011, the FDA noted that claims that AzaSite had anti-inflammatory properties had never been clinically validated. Klarity-A™ lists possible adverse effects such as eye irritation, blurred vision, contact dermatitis, corneal erosion, decreased visual acuity, dysgeusia, eye pain, facial edema, eye reactions (burning sensation, eye discharge, stinging), nasal congestion, sinusitis, swelling of the eye, and skin rash.

In contrast to commercial antibiotic formulations, the sub-antibiotic pharmaceutical formulations of this present disclosure are useful, and safe, for long-term (e.g., at least one month, years) treatment of chronic disorders of the eye that do not result from, for instance, infection or inflammation of tissue in or around the eye. The comparatively low doses of the sub-antibiotic formulations described herein, instead, alter the meibum lipid chemistry, reduce the phase transition temperature and melting point of meibum, and thereby help liquefy, loosen, or soften hardened meibum at any temperature, including at normal environmental, physiological, body, and eyelid temperatures, to ensure consistent natural meibum expression from the meibomian glands onto the tear via the blink mechanism. In so doing, the healthy and protective outermost lipid layer of tears are restored and fortified and the accelerated, premature evaporation of tears is avoided. In so doing, the symptoms of chronic DED and blepharitis associated with obstructed meibomian glands, hardened and unavailable meibum, or poor quality meibum can be alleviated. Additionally, in some embodiments, the pharmaceutical formulations can chronically maintain the quality of meibum secreted by healthy individuals, thus preventing MGD or MGD-related EDE. Previous studies have shown that antibiotic levels of azithromycin (1%) can improve the phase transition temperature of meibum lipids and lipid ordering (Foulks, et al., *Cornea*, 2010, 29(7)). Pharmaceutical formulations disclosed herein may improve the phase transition temperature of meibum lipids and lipid ordering at lower concentrations and for extended periods of time. The methods and formulations described herein may reduce a symptom of inadequate tear production or poor quality of tears. In some embodiments, a symptom of inadequate tear production or poor quality of tears may be redness, stinging, burning, itching, light sensitivity, watery eyes, blurry vision, irregularities of the ocular surface, or damage to corneal or conjunctival epithelium and tissues. In some embodiments, the sub-antiparasitic pharmaceutical formulations may address posterior blepharitis.

A pharmaceutical formulation for treating a condition of the eye may comprise a dicarboxylic acid such as azelaic acid. Azelaic acid (nonanedioic acid) is a saturated dicarboxylic acid with anti-inflammatory properties that is used in commercial formulations for the treatment of acne and rosacea. Approved commercial products such as FINACEA and AZELEX contain high concentrations (15% and 20%, respectively) of azelaic acid. Pharmaceutical formulations of this present disclosure comprising a dicarboxylic acid (e.g., azelaic acid) are useful, and safe, for long-term (e.g., at least one month, at least six months, at least one year) treatment of chronic disorders of the eye that do not result from, for instance, infection or inflammation of tissue in or around the eye. Specifically, the pharmaceutical formulations disclosed herein may act on the anterior eyelid to treat ocular conditions such as MGD, MGD-related EDE, or blepharitis in, at, or around the orifice of the meibomian glands. Dicarboxylic acids (e.g., azelaic acid) may also have anti-inflammatory, anti-oxidative, anti-bacterial, or anti-keratinizing properties that act complementary to the treatment of anterior lid conditions. Dicarboxylic acids, when used as described herein, may encourage cell turnover, promote removal of dead cells, decrease keratin at the lid margin, and/or assist in exfoliation of the lid margin, and may remedy the keratinization seen in MGD. Dicarboxylic acids may additionally function to kill demodex mites and/or promote an environment sufficiently inhospitable for demodex mites, thus decreasing the likelihood of demodex mite survival. In some embodiments, the dicarboxylic acid (e.g., azelaic acid) may address anterior blepharitis.

In the case of a dicarboxylic acid (e.g., azelaic acid), the pharmaceutical formulations described herein may comprise between about 1% and about 20% of a dicarboxylic acid (e.g., azelaic acid). In some embodiments, the pharmaceutical formulation comprises between about 1% and 5%; 5% and 10%; 10% and 15%; or 15% and 20% dicarboxylic acid (e.g., azelaic acid). In some embodiments, the pharmaceutical formulation comprises between about 1% and 2%; 2% and 20%; 2% and 18%; 2% and 16%; 2% and 14%; 2% and 12%; 2% and 10%; 2% and 8%; 2% and 6%; 2% and 4%; 4% and 20%; 4% and 18%; 4% and 16%; 4% and 14%; 4% and 12%; 4% and 10%; 4% and 8%; 4% and 6%; 6% and 20%; 6% and 18%; 6% and 16%; 6% and 14%; 6% and 12%; 6% and 10%; 6% and 8%; 8% and 20%; 8% and 18%; 8% and 16%; 8% and 14%; 8% and 12%; 8% and 10%; 10% and 20%; 10% and 18%; 10% and 16%; 10% and 14%; 10% and 12%; 12% and 20%; 12% and 18%; 12% and 16%; 12% and 14%; 14% and 20%; 14% and 18%; 14% and 16%; 16% and 20%; 16% and 18%; or 18% and 20% dicarboxylic acid (e.g., azelaic acid). In some embodiments, the pharmaceutical formulation comprises about 1%, 2%, 3%, 4%, 5%, 6%, 7%, 8%, 9%, 10%, 11%, 12%, 13%, 14%, 15%, 16%, 17%, 18%, 19%, or 20% dicarboxyclic acid (e.g., azelaic acid).

In some embodiments, a pharmaceutical formulation for treating a condition of the eye may include an antiparasitic. For instance, the antiparasitic may be an avermectin. In particular, these formulations may include a sub-antiparasitic dose of an antiparasitic such as an avermectin. "Sub-antiparasitic", as used herein, refers to an amount or concentration of antiparasitic agent that is below what is typically administered to kill or inhibit the growth or reproduction of a parasite, or an amount or concentration of antibiotic agent that is below what is clinically useful for killing or inhibiting growth or reproduction of parasites.

The sub-antiparasitic formulations disclosed herein are contrasted with commercial formulations of antibiotics that are used in ophthalmic applications. For instance, a sub-antiparasitic amount of an avermectin may be below 1%. In some embodiments, the sub-antiparasitic avermectin of the disclosed formulations may be ivermectin, selamectin, doramectin, eprinomectin, or abamectin. In some embodiments, the avermectin is ivermectin.

Notably, the sub-antiparasitic formulations disclosed herein are contrasted with commercial formulations of antiparasitics. For instance, the commercial formulation Soolantra® is a topical 1% ivermectin cream used to treat rosacea. The FDA label specifies that it should not be used for ophthalmic purposes. In one clinical trial (see https://www.accessdata.fda.gov/drugsatfda_docs/nda/2014/206255Orig1s000MedR.pdf), a 52 week open-label study with 1% ivermectin was stopped early at week 10 due to abnormal laboratory findings, namely, low neutrophil counts. Notably, lower concentrations lose efficacy toward its intended rosacea treatment (e.g., 0.1% and 0.35%). Additional safety concerns with 1% ivermectin cream include nasopharyngitis, headache, and upper respiratory tract infection.

In contrast to topical anti-parasitic formulations, the sub-antiparasitic pharmaceutical formulations of the present disclosure are useful, and safe, for long-term (e.g., at least one month, years) treatment of chronic disorders of the eye that do not result from, for instance, parasitic infection or inflammation of tissue in or around the eye. As described for the sub-antibiotic formulations above, the comparatively low doses of the sub-antiparasitic formulations described herein, instead, alter the meibum lipid chemistry and loosen or soften hardened meibum to ensure consistent natural expression from the meibomian glands. In so doing, the symptoms of chronic DED and blepharitis associated with obstructed glands, hardened and unavailable meibum, or poor quality meibum can be alleviated. Additionally, in some embodiments, the pharmaceutical formulations can chronically maintain the quality of meibum secreted by healthy individuals, thus preventing MGD or MGD-related EDE. In some embodiments, the sub-antiparasitic pharmaceutical formulations may address posterior blepharitis.

As described above, a sub-antibiotic formulation may have less than 1% of an antibiotic, and a sub-antiparasitic formulation may have less than 1% of an antiparasitic. In some embodiments, the pharmaceutical formulation comprises less than 1% azithromycin. In certain embodiments, the pharmaceutical formulation comprises 0.5% or less azithromycin. In certain embodiments, the pharmaceutical formulation comprises 0.1% or less azithromycin. In certain embodiments, the pharmaceutical formulation comprises 0.01% or less azithromycin. In certain embodiments, the pharmaceutical formulation comprises 0.001% or less azithromycin. In certain embodiments, the pharmaceutical formulation comprises about 0.5% azithromycin. In certain embodiments, the pharmaceutical formulation comprises about 0.1% azithromycin. In certain embodiments, the pharmaceutical formulation comprises about 0.01% azithromycin. In certain embodiments, the pharmaceutical formulation comprises about 0.001% azithromycin. In certain embodiments, the pharmaceutical formulation comprises between about 0.5% and about 1% azithromycin. In certain embodiments, the pharmaceutical formulation comprises between about 0.1% and about 1% azithromycin. In certain embodiments, the pharmaceutical formulation comprises between about 0.01% and about 1% azithromycin. In certain embodiments, the pharmaceutical formulation comprises between about 0.001% and about 1% azithromycin. In certain embodiments, the pharmaceutical formulation comprises between about 0.01% and about 0.1% azithromycin. In certain embodiments, the pharmaceutical formulation comprises between about 0.001% and about 0.1% azithromycin. In certain embodiments, the pharmaceutical formulation comprises between about 0.001% and about 0.01% azithromycin. In certain embodiments, the pharmaceutical formulation comprises between about 0.4% and about 0.5% azithromycin. In certain embodiments, the pharmaceutical formulation may further comprise a dicarboxylic acid (e.g., azelaic acid). The pharmaceutical formulation may, for instance, comprise any concentration of azithromycin and any concentration of a dicarboxylic acid (e.g., azelaic acid) described herein. In some embodiments, the pharmaceutical formulation comprises between about 1% and about 20% a dicarboxylic acid (e.g., azelaic acid). In some embodiments, the pharmaceutical formulation comprises between about 1% and 5%; 5% and 10%; 10% and 15%; or 15% and 20% a dicarboxylic acid (e.g., azelaic acid). In some embodiments, the pharmaceutical formulation comprises between about 1% and 2%; 2% and 20%; 2% and 18%; 2% and 16%; 2% and 14%; 2% and 12%; 2% and 10%; 2% and 8%; 2% and 6%; 2% and 4%; 4% and 20%; 4% and 18%; 4% and 16%; 4% and 14%; 4% and 12%; 4% and 10%; 4% and 8%; 4% and 6%; 6% and 20%; 6% and 18%; 6% and 16%; 6% and 14%; 6% and 12%; 6% and 10%; 6% and 8%; 8% and 20%; 8% and 18%; 8% and 16%; 8% and 14%; 8% and 12%; 8% and 10%; 10% and 20%; 10% and 18%; 10% and 16%; 10% and 14%; 10% and 12%; 12% and 20%; 12% and 18%; 12% and 16%; 12% and 14%; 14% and 20%; 14% and 18%; 14% and 16%; 16% and 20%; 16% and 18%; or 18% and 20% a dicarboxylic acid (e.g., azelaic acid). In some embodiments, the pharmaceutical formulation comprises about 1%, 2%, 3%, 4%, 5%, 6%, 7%, 8%, 9%, 10%, 11%, 12%, 13%, 14%, 15%, 16%, 17%, 18%, 19%, or 20% dicarboxyclic acid (e.g., azelaic acid).

Table 1 shows exemplary formulations of a sub-antibiotic dose of azithromycin in combination with azelaic acid.

TABLE 1

Exemplary formulations of a sub-antibiotic dose of azithromycin in combination with azelaic acid

| Sub-antibiotic dose of azithromycin | Azelaic acid |
| --- | --- |
| 0.4% azithromycin | 5% azelaic acid |
| 0.4% azithromycin | 10% azelaic acid |
| 0.4% azithromycin | 15% azelaic acid |
| 0.5% azithromycin | 5% azelaic acid |
| 0.5% azithromycin | 10% azelaic acid |
| 0.5% azithromycin | 15% azelaic acid |

In the case of sub-antiparasitic formulations, the pharmaceutical formulation may have less than 1% of an avermectin. In certain embodiments, the pharmaceutical formulation comprises 0.5% or less of an avermectin. In certain embodiments, the pharmaceutical formulation comprises 0.1% or less of an avermectin. In certain embodiments, the pharmaceutical formulation comprises 0.01% or less of an avermectin. In certain embodiments, the pharmaceutical formulation comprises 0.001% or less of an avermectin. In certain embodiments, the pharmaceutical formulation comprises about 0.5% of an avermectin. In certain embodiments, the pharmaceutical formulation comprises about 0.1% of an avermectin. In certain embodiments, the pharmaceutical formulation comprises about 0.01% of an avermectin. In certain embodiments, the pharmaceutical formulation comprises about 0.001% of an avermectin. In certain embodiments, the pharmaceutical formulation comprises between about 0.5% and about 1% of an avermectin. In certain embodiments, the pharmaceutical formulation comprises between about 0.1% and about 1% of an avermectin. In certain embodiments, the pharmaceutical formulation comprises between about 0.01% and about 1% of an avermectin. In certain embodiments, the pharmaceutical formulation comprises between about 0.001% and about 1% of an avermectin. In certain embodiments, the pharmaceutical formulation comprises between about 0.01% and about 0.1% of an avermectin. In certain embodiments, the pharmaceutical formulation comprises between about 0.001% and about 0.1% of an avermectin. In certain embodiments, the pharmaceutical formulation comprises between about 0.001% and about 0.01% of an avermectin. In certain embodiments, the pharmaceutical formulation may further comprise a dicarboxylic acid (e.g., azelaic acid). The pharmaceutical formulation may, for instance, comprise any concentration of an avermectin and any concentration of a dicarboxylic acid (e.g., azelaic acid) described herein. In some embodiments, the pharmaceutical formulation comprises between about 1% and about 20% dicarboxylic acid (e.g., azelaic acid). In some embodiments, the pharmaceutical formulation comprises between about 1% and 5%; 5% and 10%; 10% and 15%; or 15% and 20% dicarboxylic acid (e.g., azelaic acid). In some embodiments, the pharmaceutical formulation comprises between about 1% and 2%; 2% and 20%; 2% and 18%; 2% and 16%; 2% and 14%; 2% and 12%; 2% and 10%; 2% and 8%; 2% and 6%; 2% and 4%; 4% and 20%; 4% and 18%; 4% and 16%; 4% and 14%; 4% and 12%; 4% and 10%; 4% and 8%; 4% and 6%; 6% and 20%; 6% and 18%; 6% and 16%; 6% and 14%; 6% and 12%; 6% and 10%; 6% and 8%; 8% and 20%; 8% and 18%; 8% and 16%; 8% and 14%; 8% and 12%; 8% and 10%; 10% and 20%; 10% and 18%; 10% and 16%; 10% and 14%; 10% and 12%; 12% and 20%; 12% and 18%; 12% and 16%; 12% and 14%; 14% and 20%; 14% and 18%; 14% and 16%; 16% and 20%; 16% and 18%; or 18% and 20% a dicarboxylic acid (e.g., azelaic acid). In some embodiments, the pharmaceutical formulation comprises about 1%, 2%, 3%, 4%, 5%, 6%, 7%, 8%, 9%, 10%, 11%, 12%, 13%, 14%, 15%, 16%, 17%, 18%, 19%, or 20% dicarboxyclic acid (e.g., azelaic acid).

A formulation of a sub-antibiotic dose of an antibiotic, or a sub-antiparasitic dose of an anti-parasitic, as described above, may be on their own sufficient, and safe, for treating a chronic condition of the eye. However, in some instances it might be beneficial to apply formulations that combine both an antiparasitic and an antibiotic in order to achieve a more robust effect. This increased effect might be a result of synergy between the two agents in their ability to increase the amount and/or quality of meibum produced. Similarly, such a synergistic effect may be obtained by combining azithromycin with a dicarboxylic acid (e.g., azelaic acid) or ivermectin with a dicarboxylic acid (e.g., azelaic acid).

For instance, in some embodiments, the pharmaceutical formulation may have both azithromycin and an avermectin. In certain embodiments, the pharmaceutical formulation comprises a sub-antibiotic dose of azithromycin and further comprises an avermectin. In certain embodiments, the pharmaceutical formulation comprises a sub-antibiotic dose of azithromycin and further comprises 1% or more of an avermectin. In certain embodiments, the pharmaceutical formulation comprises a sub-antiparasitic dose of an avermectin and further comprises 1% or more azithromycin. In some embodiments, the pharmaceutical formulation comprises a sub-antibiotic dose of azithromycin and further comprises a sub-antiparasitic dose of an avermectin. In some embodiments, the pharmaceutical formulation comprises a sub-antibiotic dose of azithromycin, a sub-antiparasitic dose of an avermectin, and a dose of a dicarboxylic acid (e.g., azelaic acid).

The formulations of the present disclosure can be delivered by a topical route to the external surface of the eyelid. For instance, the pharmaceutical formulations may be applied (e.g., administered) via applicator sticks, contact lenses, ocular inserts, cul-de-sac inserts, fornix inserts, as solutions, suspensions, emulsions, gels, creams, ointments, pastes, jellies, paints, powders, sprays, drops, and aerosols. The formulations of the present disclosure may additionally include components to provide sustained release and/or comfort. Such components include high molecular weight, anionic mucomimetic polymers, gelling polysaccharides and finely-divided drug carrier substrates. Formulations may additionally be loaded onto a patch with an absorbable adhesive, or a fully or partially bioabsorbable patch, that is applied to one or more of the eyelids.

One advantage of the pharmaceutical formulations disclosed herein is that they may be applied directly to an eyelid, rather than be applied systemically. Application to the eyelids allows the formulation to most directly reach the meibomian glands, where meibum amount and/or quality can be improved. To assist in penetration of the sub-antibiotic dose of azithromycin, a sub-antiparasitic dose of an avermectin, and/or a dicarboxylic acid (e.g., azelaic acid) through the eyelid to reach the meibomian glands, the pharmaceutical formulation may have at least one skin penetration enhancer. In some embodiments, the skin penetration enhancer is selected from polyethylene glycol, propylene glycol, sodium laurel sulfate, and a ceramide. In certain embodiments, the pharmaceutical formulation comprises about 0.1% to about 5% of the skin penetration enhancer. In certain embodiments, the pharmaceutical formulation comprises about 0.1% to about 1% of the skin penetration enhancer. In certain embodiments, the pharmaceutical formulation comprises about 0.1% to about 0.25% of the skin penetration enhancer. In certain embodiments, the pharmaceutical formulation comprises about 1% to about 5% of the skin penetration enhancer. In certain embodiments, the pharmaceutical formulation comprises about 1% to about 4% of the skin penetration enhancer. In certain embodiments, the pharmaceutical formulation comprises about 1% to about 3% of the skin penetration enhancer. In certain embodiments, the pharmaceutical formulation comprises about 1% to about 2% of the skin penetration enhancer. In certain embodiments, the pharmaceutical formulation comprises about 2% to about 5% of the skin penetration enhancer. In certain embodiments, the pharmaceutical formulation comprises about 2% to about 4% of the skin penetration enhancer. In certain embodiments, the pharmaceutical formulation comprises about 2% to about 3% of the skin penetration enhancer. In certain embodiments, the pharmaceutical formulation comprises about 3% to about 5% of the skin penetration enhancer. In certain embodiments, the pharmaceutical formulation comprises about 3% to about 4% of the skin penetration enhancer.

Exemplary formulations of a sub-antibiotic dose of azithromycin in combination with a skin penetration enhancer are shown in Table 2.

TABLE 2

| Exemplary formulations of a sub-antibiotic dose of azithromycin in combination with a skin penetration enhancer | |
|---|---|
| Azithromycin Composition | Skin Penetration Enhancer |
| Sub-antibiotic azithromycin | 0.5-4% polyethylene glycol |
| Sub-antibiotic azithromycin | 0.5-4% propylene glycol |
| Sub-antibiotic azithromycin | 1% sodium laurel sulfate and a ceramide |
| Sub-antibiotic azithromycin | 0.5-4% polyethylene glycol, 0.5-4% propylene glycol, 1% sodium laurel sulfate, and a ceramide |
| Sub-antibiotic azithromycin | 0.5% polyethylene glycol and 0.5% propylene glycol |
| Sub-antibiotic azithromycin | 0.25% polyethylene glycol and 0.25% propylene glycol |

Exemplary formulations of azelaic acid in combination with a skin penetration enhancer are shown in Table 3.

TABLE 3

| Exemplary formulations of a sub-antibiotic dose of azelaic acid in combination with a skin penetration enhancer | |
|---|---|
| Azelaic Acid Composition | Skin Penetration Enhancer |
| 5% azelaic acid | 0.5-4% polyethylene glycol |
| 5% azelaic acid | 0.5-4% propylene glycol |
| 5% azelaic acid | 1% sodium laurel sulfate and a ceramide |
| 5% azelaic acid | 0.5-4% polyethylene glycol, 0.5-4% propylene glycol, 1% sodium laurel sulfate, and a ceramide |
| 5% azelaic acid | 0.5% polyethylene glycol and 0.5% propylene glycol |
| 5% azelaic acid | 0.25% polyethylene glycol and 0.25% propylene glycol |
| 10% azelaic acid | 0.5-4% polyethylene glycol |
| 10% azelaic acid | 0.5-4% propylene glycol |
| 10% azelaic acid | 1% sodium laurel sulfate and a ceramide |
| 10% azelaic acid | 0.5-4% polyethylene glycol, 0.5-4% propylene glycol, 1% sodium laurel sulfate, and a ceramide |
| 10% azelaic acid | 0.5% polyethylene glycol and 0.5% propylene glycol |
| 10% azelaic acid | 0.25% polyethylene glycol and 0.25% propylene glycol |
| 15% azelaic acid | 0.5-4% polyethylene glycol |
| 15% azelaic acid | 0.5-4% propylene glycol |
| 15% azelaic acid | 1% sodium laurel sulfate and a ceramide |
| 15% azelaic acid | 0.5-4% polyethylene glycol, 0.5-4% propylene glycol, 1% sodium laurel sulfate, and a ceramide |
| 15% azelaic acid | 0.5% polyethylene glycol and 0.5% propylene glycol |
| 15% azelaic acid | 0.25% polyethylene glycol and 0.25% propylene glycol |

Exemplary formulations of a sub-antibiotic dose of an avermectin in combination with a skin penetration enhancer are shown in Table 4.

TABLE 4

| Exemplary formulations of a sub-antiparasitic dose of an avermectin in combination with a skin penetration enhancer | |
|---|---|
| Avermectin Composition | Skin Penetration Enhancer |
| Sub-antiparasitic ivermectin | 0.5-4% polyethylene glycol |
| Sub-antiparasitic ivermectin | 0.5-4% propylene glycol |
| Sub-antiparasitic ivermectin | 1% sodium laurel sulfate and a ceramide |
| Sub-antiparasitic ivermectin | 0.5-4% polyethylene glycol, 0.5-4% propylene glycol, 1% sodium laurel sulfate, and a ceramide |
| Sub-antiparasitic ivermectin | 0.5% polyethylene glycol and 0.5% propylene glycol |
| Sub-antiparasitic ivermectin | 0.25% polyethylene glycol and 0.25% propylene glycol |

In some embodiments, the formulations described herein may contain at least one polyol. Therefore, adding a polyol to a formulation described herein may increase solubility of one or more component described herein (e.g., azithromycin, azelaic acid). In some embodiments, the polyol is propylene glycol, polyethylene glycol, glycerol, erythritol, mannitol, or sorbitol. In certain embodiments, the pharmaceutical formulation comprises about 0.1% to about 20% of the polyol. In certain embodiments, the pharmaceutical formulation comprises about 0.1% to about 15% of the polyol. In certain embodiments, the pharmaceutical formulation comprises about 0.1% to about 10% of the polyol. In certain embodiments, the pharmaceutical formulation comprises about 0.1% to about 5% of the polyol. In certain embodiments, the pharmaceutical formulation comprises about 1% to about 20% of the polyol. In certain embodiments, the pharmaceutical formulation comprises about 1% to about 15% of the polyol. In certain embodiments, the pharmaceutical formulation comprises about 1% to about 10% of the polyol. In certain embodiments, the pharmaceutical formulation comprises about 1% to about 5% of the polyol. In certain embodiments, the pharmaceutical formulation comprises about 1% to about 4%; about 4% to about 20%; about 4% to about 16%; about 4% to about 12%; about 4% to about 8%; 8% to about 20%; about 8% to about 16%; about 8% to about 12%; about 12% to about 20%; about 12% to about 16%; or about 16% to about 20%; of the polyol. In certain embodiments, the pharmaceutical formulation comprises about 1%, 2%, 3%, 4%, 5%, 6%, 7%, 8%, 9%, 10%, 11%, 12%, 13%, 14%, 15%, 16%, 17%, 18%, 19%, or 20% of the polyol.

Exemplary formulations of a sub-antibiotic dose of azithromycin and azelaic acid in combination with a polyol are shown in Table 5.

TABLE 5

| Exemplary formulations of a sub-antibiotic dose of azithromycin and azelaic acid in combination with a polyol suitable for treating conditions of the eye | | |
|---|---|---|
| Azithromycin | Azelaic acid | Polyol |
| About 0.1%-0.5% azithromycin | About 1%-20% azelaic acid | About 1%-10% propylene glycol |
| About 0.1%-0.5% azithromycin | About 5%-20% azelaic acid | About 1%-10% propylene glycol |
| About 0.4%-0.5% azithromycin | About 5%-15% azelaic acid | About 1%-10% propylene glycol |
| About 0.4% azithromycin | About 10% azelaic acid | About 8% propylene glycol |

In some instances, it is beneficial to administer a sub-antibiotic dose of azithromycin, a sub-antiparasitic dose of an avermectin, and/or a dicarboxylic acid (e.g., azelaic acid) together with an immunosuppressant. In this way, improvement of meibum amount and/or quality may be achieved by the azithromycin, avermectin, and/or a dicarboxylic acid (e.g., azelaic acid), and additional improvement in inflammatory aspects of the condition of the eye may be concomitantly achieved by the immunosuppressant. Disclosed formulations may be useful in treating ADDE and EDE simultaneously. In some embodiments, the pharmaceutical formulation comprises an immunosuppressant. In certain embodiments, the immunosuppressant is selected from the group consisting of cyclosporine, tacrolimus, and lifitegrast. In certain embodiments, the immunosuppressant is cyclosporine. In certain embodiments, the immunosuppressant is tacrolimus. In certain embodiments, the immunosuppressant is lifitegrast. In certain embodiments, the pharmaceutical formulation comprises less than about 1% of an immunosuppressant. In certain embodiments, the pharmaceutical formulation comprises about 0.01% to about 5% of an immunosuppressant. In certain embodiments, the pharmaceutical formulation comprises about 0.01% to about 0.1% of an immunosuppressant. In certain embodiments, the pharmaceutical formulation comprises about 0.01% to about 0.05% of an immunosuppressant. In certain embodiments, the pharmaceutical formulation comprises about 0.05% to about 0.1% of an immunosuppressant. In certain embodiments, the pharmaceutical formulation comprises about 0.1% to about 5% of an immunosuppressant. In certain embodiments, the pharmaceutical formulation comprises about 1% of an immunosuppressant. In certain embodiments, the pharmaceutical formulation comprises about 5% of an immunosuppressant.

In some embodiments, the pharmaceutical formulation comprises one or more additional agent selected from the group consisting of brimonidine, isotretinoin, cyclosporine, hypochlorous acid, and tea tree oil.

Additionally or alternatively, the pharmaceutical formulations disclosed herein may be suitable for treating dermatologic conditions, including rosacea and acne, independent of age (i.e., for all age groups).

In some embodiments of the pharmaceutical formulation disclosed herein, the formulation may contain one or more additional pharmaceutically acceptable carriers. Conventional procedures for the selection and preparation of suitable pharmaceutical formulations are described in, for example, "Pharmaceuticals—The Science of Dosage Form Designs," M. E. Aulton, Churchill Livingstone, 1988, which is hereby incorporated by reference in its entirety.

The term "carrier", as used herein, may encompass carriers, excipients, and diluents and may mean a material, formulation or vehicle, such as a liquid or solid filler, diluent, excipient, solvent or encapsulating material, involved in carrying or transporting a pharmaceutical agent, such as one or more crystalline forms of the disclosure, from one organ, or portion of the body, to another organ, or portion of the body of a subject. Carriers should be selected on the basis of compatibility and the release profile properties of the desired dosage form. Exemplary carrier materials may include, e.g., binders, suspending agents, disintegration agents, filling agents, surfactants, solubilizers, stabilizers, lubricants, wetting agents, diluents, spray-dried dispersions, and the like. See, e.g., Hoover, John E., *Remington's Pharmaceutical Sciences*, Mack Publishing Co., Easton, Pa. 1975.

In some embodiments, the formulations described herein may contain mineral oil and/or petrolatum.

In some embodiments, the agents described herein, alone or as part of a pharmaceutical formulation, are also understood to include any pharmaceutically acceptable salt, solvate, tautomer, isotope, or isomer thereof.

Methods of Treating a Disorder

As described above, the formulations disclosed herein can be applied safely and chronically to treat disorders of the eye. Unlike commercially available, higher concentration antibiotics or antiparasitic formulations indicated for their intended antibiotic or antiparasitic purposes, which can only be applied to the eye acutely, or cannot be applied to the eye at all, the present sub-antibiotic and sub-antiparasitic formulations, and formulations comprising a dicarboxylic acid (e.g., azelaic acid), target the meibomian glands directly, restore natural meibum lipid chemistry, restore natural meibum melting temperatures, and thereby improve the amount and/or quality of meibum produced and available to coat the outermost lipid layer of tears chronically. Methods described herein may reduce a symptom of inadequate tear production or poor quality of tears. In some embodiments, a symptom of inadequate tear production or poor quality of tears may be redness, stinging, burning, itching, light sensitivity, watery eyes, blurry vision, irregularities of the ocular surface, or damage to corneal or conjunctival epithelium and tissues. Formulations of the present invention may be safely applied daily for extended periods of time.

Chronic application could, for instance, involve application of the disclosed pharmaceutical formulation over the course of at least a month. Notably, the formulations could be applied for significantly longer than one month. For instance, the formulations may be applied for at least 2 months, 6 months, 1 years, 2 years, 3 years, 4 years, 5 years, 10 years, or longer. This directly benefits patients who suffer from chronic or congenital DED or blepharitis, or who otherwise need improved meibum quality, and is not achievable with existing commercial formulations discussed previously.

Specifically, the pharmaceutical formulations disclosed herein may be administered (e.g., applied) daily for at least 1 month. In some embodiments, the pharmaceutical formulation is administered daily for at least 2 months. In some embodiments, the pharmaceutical formulation is administered daily for at least 3 months. In some embodiments, the pharmaceutical formulation is administered daily for at least 4 months. In some embodiments, the pharmaceutical formulation is administered daily for at least 5 months. In some embodiments, the pharmaceutical formulation is administered daily for at least 6 months. In some embodiments, the pharmaceutical formulation is administered daily for at least 7 months. In some embodiments, the pharmaceutical formulation is administered daily for at least 8 months. In some embodiments, the pharmaceutical formulation is administered daily for at least 9 months. In some embodiments, the pharmaceutical formulation is administered daily for at least 10 months. In some embodiments, the pharmaceutical formulation is administered daily for at least 11 months. In some embodiments, the pharmaceutical formulation is administered daily for at least 1 year. In some embodiments, the pharmaceutical formulation is administered daily for at least 2 years. In some embodiments, the pharmaceutical formulation is administered daily for at least 3 years. In some embodiments, the pharmaceutical formulation is administered daily for at least 4 months. In some embodiments, the pharmaceutical formulation is administered daily for at least 5 years.

The pharmaceutical formulations disclosed herein may also be administered every other day. In some embodiments, the pharmaceutical formulation is administered daily every other week (e.g., one week of administration, followed by one week without administration). In some embodiments, the pharmaceutical formulation is administered daily every other month.

In the methods disclosed herein, the daily administration of a pharmaceutical formulation may mean once per day (i.e., once daily). In some cases, it might be beneficial to apply the pharmaceutical formulation more than once per day. In these cases, daily could mean twice a day (i.e., twice daily), three times a day, four times a day, or more.

Generally, a method for treating a condition of the eye in a subject in need thereof may include administering one or more compounds or pharmaceutical formulations described herein. In certain embodiments, a method for treating dry eye disease in a subject in need thereof may include administering one or more compounds or pharmaceutical formulations described herein. In some embodiments, a method for treating blepharitis in a subject in need thereof may include administering one or more compounds or pharmaceutical formulations described herein In some embodiments, provided herein is the use of one or more compounds or pharmaceutical formulations described herein in the manufacture of a medicament for treating a disorder. In some embodiments, provided herein is the use of one or more compounds or pharmaceutical formulations described herein in the manufacture of a medicament for treating a condition of the eye. In some embodiments, provided herein is the use of one or more compounds or pharmaceutical formulations described herein in the manufacture of a medicament for treating dry eye disease. In some embodiments, provided herein is the use of one or more pharmaceutical compounds or pharmaceutical formulations described herein in the manufacture of a medicament for treating blepharitis. In some embodiments, provided herein is the use of one or more compounds or pharmaceutical formulations described herein in the manufacture of a medicament for increasing secretion of meibum.

In some embodiments, provided herein is the use of one or more compounds or pharmaceutical formulations described herein as a medicament for treating a disorder. In some embodiments, provided herein is the use of one or more compounds or pharmaceutical formulations described herein as a medicament for treating a condition of the eye. In some embodiments, provided herein is the use of one or more compounds or pharmaceutical formulations described herein as a medicament for treating dry eye disease. In some embodiments, provided herein is the use of one or more pharmaceutical compounds or pharmaceutical formulations described herein as a medicament for treating blepharitis. In some embodiments, provided herein is the use of one or more compounds or pharmaceutical formulations described herein as a medicament for increasing secretion of meibum.

In some embodiments, provided herein is the use of one or more compounds or pharmaceutical formulations described herein for treating a disorder. In some embodiments, provided herein is the use of one or more compounds or pharmaceutical formulations described herein for treating a condition of the eye. In some embodiments, provided herein is the use of one or more compounds or pharmaceutical formulations described herein for treating dry eye disease. In some embodiments, provided herein is the use of one or more pharmaceutical compounds or pharmaceutical formulations described herein for treating blepharitis. In some embodiments, provided herein is the use of one or more compounds or pharmaceutical formulations described herein for increasing secretion of meibum.

The methods described herein might be useful in treating any condition of the eye for which the amount of meibum produced, or for which the quality of meibum produced, is reduced. Generally, this could be achieved through the application of a sub-antibiotic dose of an antibiotic. In some embodiments, provided herein is a method for treating a condition of the eye in a subject in need thereof. In some embodiments, provided herein is a method for treating a condition of the eye in a subject in need thereof, comprising administering to the subject a pharmaceutical formulation comprising a sub-antibiotic dose of an antibiotic. In some embodiments, provided herein is a method for treating a condition of the eye in a subject in need thereof, comprising administering to the subject a pharmaceutical formulation comprising a sub-antibiotic dose of an antibiotic, wherein; (a) the pharmaceutical formulation is administered to the eyelid, and (b) the pharmaceutical formulation is administered daily for at least 1 month.

Similarly, general conditions of the eye for which meibum quantity or quality is impacted may be treated by the methods disclosed herein, whereby a sub-antiparasitic dose of an antiparasitic is applied. In some embodiments, provided herein is a method for treating a condition of the eye in a subject in need thereof, comprising administering to the subject a pharmaceutical formulation comprising a sub-antiparasitic dose of an antiparasitic. In some embodiments, provided herein is a method for treating a condition of the eye in a subject in need thereof, comprising administering to the subject a pharmaceutical formulation comprising a sub-antiparasitic dose of an antiparasitic, wherein; (a) the pharmaceutical formulation is administered to the eyelid, and (b) the pharmaceutical formulation is administered daily for at least 1 month.

Similarly, general conditions of the eye for which meibum quantity and/or quality is impacted may be treated by the methods disclosed herein, whereby a dicarboxylic acid (e.g., azelaic acid) is applied. In some embodiments, provided herein is a method for treating a condition of the eye in a subject in need thereof, comprising administering to the subject a pharmaceutical formulation comprising a dicarboxylic acid (e.g., azelaic acid). In some embodiments, provided herein is a method for treating a condition of the eye in a subject in need thereof, comprising administering to the subject a pharmaceutical formulation comprising a dicarboxylic acid (e.g., azelaic acid), wherein; (a) the pharmaceutical formulation is administered to the eyelid, and (b) the pharmaceutical formulation is administered daily for at least 1 month.

In some embodiments, the antibiotic applied in a sub-antibiotic dose may be azithromycin. In some embodiments, provided herein is a method for treating a condition of the eye in a subject in need thereof. In some embodiments, provided herein is a method for treating a condition of the eye in a subject in need thereof, comprising administering to the subject a pharmaceutical formulation comprising a sub-antibiotic dose of azithromycin. In some embodiments, provided herein is a method for treating a condition of the eye in a subject in need thereof, comprising administering to the subject a pharmaceutical formulation comprising a sub-antibiotic dose of azithromycin, wherein; (a) the pharmaceutical formulation is administered to the eyelid, and (b) the pharmaceutical formulation is administered daily for at least 1 month. In some embodiments, the sub-antibiotic dose of azithromycin may address posterior blepharitis.

Alternatively, the antiparasitic applied in a sub-antiparasitic dose may be an avermectin. In some embodiments, provided herein is a method for treating a condition of the eye in a subject in need thereof, comprising administering to the subject a pharmaceutical formulation comprising a sub-antiparasitic dose of an avermectin. In some embodiments, provided herein is a method for treating a condition of the eye in a subject in need thereof, comprising administering to the subject a pharmaceutical formulation comprising a sub-antiparasitic dose of an avermectin, wherein; (a) the pharmaceutical formulation is administered to the eyelid, and (b) the pharmaceutical formulation is administered daily for at least 1 month. In some embodiments, the sub-antiparasitic dose of an avermectin may address posterior blepharitis.

A method for treating a condition of the eye comprising administering to the subject a pharmaceutical formulation comprising: a) a sub-antibiotic dose of azithromycin; b) a sub-antiparasitic dose of an avermectin; c) a sub-antibiotic dose of azithromycin and a sub-antiparasitic dose of an avermectin; d) a sub-antibiotic dose of azithromycin or a sub-antiparasitic dose of an avermectin, and further comprising an immunosuppressant; e) a sub-antibiotic dose of azithromycin or a sub-antiparasitic dose of an avermectin, and further comprising azelaic acid; or f) azelaic acid. In some embodiments, the pharmaceutical formulation is applied to the eyelid daily for at least 1 month. In some embodiments of any of the methods described herein, the condition of the eye is one or more of dry eye disease, blepharitis, and meibomian gland dysfunction.

As described above, DED can result from or be caused by negatively impacted meibum amount or quality. DED therefore can be treated by the formulations of this invention, via the improvement of meibum amount or quality. In some embodiments, provided herein is a method for treating dry eye disease in a subject in need thereof. In some embodiments, provided herein is a method for treating dry eye disease in a subject in need thereof, comprising administering to the subject a pharmaceutical formulation comprising a sub-antibiotic dose of an antibiotic. In some embodiments, provided herein is a method for treating dry eye disease in a subject in need thereof, comprising administering to the subject a pharmaceutical formulation comprising a sub-antibiotic dose of an antibiotic, wherein; (a) the pharmaceutical formulation is administered to the eyelid, and (b) the pharmaceutical formulation is administered daily for at least 1 month. In some embodiments, provided herein is a method for treating dry eye disease by lowering the melting temperature of meibum. Methods of treating dry eye disease in a subject in need thereof may comprise administering a pharmaceutical formulation comprising a sub-antibiotic dose of an antibiotic, and further comprising a dicarboxylic acid (e.g., azelaic acid).

Alternatively, but via similar mechanisms, DED can be treated using sub-antiparasitic doses of antiparasitics. In some embodiments, provided herein is a method for treating dry eye disease in a subject in need thereof, comprising administering to the subject a pharmaceutical formulation comprising a sub-antiparasitic dose of an antiparasitic. In some embodiments, provided herein is a method for treating dry eye disease in a subject in need thereof, comprising administering to the subject a pharmaceutical formulation comprising a sub-antiparasitic dose of an antiparasitic, wherein; (a) the pharmaceutical formulation is administered to the eyelid, and (b) the pharmaceutical formulation is administered daily for at least 1 month. Methods of treating dry eye disease in a subject in need thereof may comprise administering a pharmaceutical formulation comprising a sub-antiparasitic dose of an antiparasitic and a dicarboxylic acid (e.g., azelaic acid).

In some embodiments, provided herein is a method for treating dry eye disease in a subject in need thereof. In some embodiments, provided herein is a method for treating dry eye disease in a subject in need thereof, comprising administering to the subject a pharmaceutical formulation comprising a sub-antibiotic dose of azithromycin. In some embodiments, provided herein is a method for treating dry eye disease in a subject in need thereof, comprising administering to the subject a pharmaceutical formulation comprising a sub-antibiotic dose of azithromycin, wherein; (a) the pharmaceutical formulation is administered to the eyelid, and (b) the pharmaceutical formulation is administered daily for at least 1 month. Methods of treating dry eye disease in a subject in need thereof may comprise administering a pharmaceutical formulation comprising a sub-antibiotic dose of azithromycin and a dicarboxylic acid (e.g., azelaic acid).

In some embodiments, the methods for treating dry eye disease disclosed herein comprise administering to an external surface of an eyelid of a subject a pharmaceutical formulation described herein, wherein administering the pharmaceutical formulation reduces a condition of dry eye disease. In some embodiments, a condition of dry eye disease may be meibomian gland dysfunction, redness, stinging, burning, itching, light sensitivity, watery eyes, blurry vision, irregularities of the ocular surface, or damage to corneal or conjunctival epithelium and tissues.

In some embodiments, provided herein is a method for treating dry eye disease in a subject in need thereof, comprising administering to the subject a pharmaceutical formulation comprising a sub-antiparasitic dose of an avermectin. In some embodiments, provided herein is a method for treating dry eye disease in a subject in need thereof, comprising administering to the subject a pharmaceutical formulation comprising a sub-antiparasitic dose of an avermectin, wherein; (a) the pharmaceutical formulation is administered to the eyelid, and (b) the pharmaceutical formulation is administered daily for at least 1 month. In some embodiments, the avermectin is ivermectin.

In some embodiments, provided herein is a method for treating dry eye disease in a subject in need thereof. In some embodiments, provided herein is a method for treating dry eye disease in a subject in need thereof, comprising administering to the subject a pharmaceutical formulation comprising a dicarboxylic acid (e.g., azelaic acid). In some embodiments, provided herein is a method for treating dry eye disease in a subject in need thereof, comprising administering to the subject a pharmaceutical formulation comprising a dicarboxylic acid (e.g., azelaic acid), wherein; (a) the pharmaceutical formulation is administered to the eyelid, and (b) the pharmaceutical formulation is administered daily for at least 1 month Methods for treating dry eye disease described herein may benefit from alternating administration of a two or more pharmaceutical formulations described herein. Thus, in some embodiments, a method for treating dry eye disease in a subject in need thereof, comprises alternating administration of a first pharmaceutical formulation and a second pharmaceutical formulation to the eyelid. In some embodiments, the first pharmaceutical formulation comprises a sub-antibiotic dose of azithromycin and is applied daily and the second pharmaceutical formulation comprises a sub-antiparasitic dose of an avermectin and is applied daily. In some embodiments, the first pharmaceutical formulation comprises a sub-antibiotic dose of azithromycin and is applied daily and the second pharmaceutical formulation comprises a dicarboxylic acid (e.g., azelaic acid) and is applied daily. In some embodiments, the first pharmaceutical formulation comprises a sub-antiparasitic dose of ivermectin and is applied daily and the second pharmaceutical formulation comprises a dicarboxylic acid (e.g., azelaic acid) and is applied daily.

Administration of the two pharmaceutical formulations may be alternated daily, weekly, monthly, or every 2, 3, 4, 5, 6, 7, 8, 9, 10, 11, or 12 months. In some embodiments, the alternating administration comprises alternating the first and second pharmaceutical formulations daily (e.g., administering a first pharmaceutical formulation to the eyelid on day 1, administering a second pharmaceutical formulation to the eyelid on day 2, administering the first pharmaceutical formulation to the eyelid on day 3, and so on). In some embodiments, the alternating administration comprises alternating the first and second pharmaceutical formulations monthly (e.g., administering a first pharmaceutical formulation to the eyelid as described herein for a first month, administering a second pharmaceutical formulation to the eyelid as described herein for a second month, administering the first pharmaceutical formulation to the eyelid as described herein for a third month, and so on). In some embodiments, the alternating administration comprises alternating the first and second pharmaceutical formulations every two months.

As described previously, DED can be described as an umbrella term encompassing several sub-disorders. In some embodiments, the dry eye disease is ADDE. In some embodiments, the dry eye disease is EDE. In some embodiments, the dry eye disease is ADDE and EDE. The methods for treating dry eye disease disclosed herein may treat ADDE and EDE simultaneously.

DED is sometimes associated with underlying factors. One of these factors may be age. In certain embodiments, the dry eye disease is associated with biological sex. In certain embodiments, the dry eye disease is associated with an autoimmune disease. In certain embodiments, the dry eye disease is associated with medications taken for other indications. In certain embodiments, the dry eye disease is associated with the use of medical devices. In certain embodiments, the dry eye disease is associated with contact lenses. In certain embodiments, the dry eye disease is associated with environment. In certain embodiments, the dry eye disease is associated with laser eye surgery. In certain embodiments, the dry eye disease is associated with cataract surgery. In certain embodiments, the dry eye disease is associated with smoking. In certain embodiments, the dry eye disease is associated with overuse of screens, such as those of smart phones, computers, tablets, and the like. In some embodiments, the dry eye disease is associated with a mucin deficiency.

In general, the methods disclosed herein may involve application of a sub-antibiotic dose of an antibiotic, useful for treating blepharitis in a subject in need thereof. In some embodiments, provided herein is a method for treating blepharitis in a subject in need thereof, comprising administering to the subject a pharmaceutical formulation comprising a sub-antibiotic dose of an antibiotic. In some embodiments, provided herein is a method for treating blepharitis in a subject in need thereof, comprising administering to the subject a pharmaceutical formulation comprising a sub-antibiotic dose of an antibiotic, wherein; (a) the pharmaceutical formulation is administered to the eyelid, and (b) the pharmaceutical formulation is administered daily for at least 1 month. Methods of treating blepharitis in a subject in need thereof may comprise administering a pharmaceutical formulation comprising a sub-antibiotic dose of an antibiotic, further comprising a dicarboxylic acid (e.g., azelaic acid).

Alternatively, a method for treating blepharitis in a subject in need thereof may involve administering to the subject a pharmaceutical formulation comprising a sub-antiparasitic dose of an antiparasitic. In some embodiments, provided herein is a method for treating blepharitis in a subject in need thereof, comprising administering to the subject a pharmaceutical formulation comprising a sub-antiparasitic dose of an antiparasitic, wherein; (a) the pharmaceutical formulation is administered to the eyelid, and (b) the pharmaceutical formulation is administered daily for at least 1 month. Methods of treating blepharitis in a subject in need thereof may comprise administering a pharmaceutical formulation comprising a sub-antiparasitic dose of an antiparasitic, further comprising a dicarboxylic acid (e.g., azelaic acid).

Additionally, a method for treating blepharitis in a subject in need thereof may involve administering to the subject a pharmaceutical formulation comprising a dicarboxylic acid (e.g., azelaic acid). In some embodiments, provided herein is a method for treating blepharitis in a subject in need thereof, comprising administering to the subject a pharmaceutical formulation comprising a dicarboxylic acid (e.g., azelaic acid), wherein; (a) the pharmaceutical formulation is administered to the eyelid, and (b) the pharmaceutical formulation is administered daily for at least 1 month.

Methods for treating blepharitis described herein may benefit from alternating administration of a two or more pharmaceutical formulations described herein. Thus, in some embodiments, a method for treating blepharitis in a subject in need thereof, comprises alternating administration of a first pharmaceutical formulation and a second pharmaceutical formulation to the eyelid. In some embodiments, the first pharmaceutical formulation comprises a sub-antibiotic dose of azithromycin and is applied daily and the second pharmaceutical formulation comprises a sub-antiparasitic dose of an avermectin and is applied daily. In some embodiments, the first pharmaceutical formulation comprises a sub-antibiotic dose of azithromycin and is applied daily and the second pharmaceutical formulation comprises a sub-antiparasitic dose of a dicarboxylic acid (e.g., azelaic acid) and is applied daily. In some embodiments, the first pharmaceutical formulation comprises a sub-antiparasitic dose of ivermectin and is applied daily and the second pharmaceutical formulation comprises a sub-antiparasitic dose of a dicarboxylic acid (e.g., azelaic acid) and is applied daily. Administration of the two pharmaceutical formulations may be alternated daily, weekly, monthly, or every 2, 3, 4, 5, 6, 7, 8, 9, 10, 11, or 12 months. In some embodiments, the alternating administration comprises alternating the first and second pharmaceutical formulations daily. In some embodiments, the alternating administration comprises alternating the first and second pharmaceutical formulations monthly. In some embodiments, the alternating administration comprises alternating the first and second pharmaceutical formulations every two months.

In some embodiments, the antibiotic applied in a sub-antibiotic dose to treat blepharitis may be azithromycin. In some embodiments, provided herein is a method for treating blepharitis in a subject in need thereof. In some embodiments, provided herein is a method for treating blepharitis in a subject in need thereof, comprising administering to the subject a pharmaceutical formulation comprising a sub-antibiotic dose of azithromycin. In some embodiments, provided herein is a method for treating blepharitis in a subject in need thereof, comprising administering to the subject a pharmaceutical formulation comprising a sub-antibiotic dose of azithromycin, wherein; (a) the pharmaceutical formulation is administered to the eyelid, and (b) the pharmaceutical formulation is administered daily for at least 1 month. Methods of treating blepharitis in a subject in need thereof may comprise administering a pharmaceutical formulation comprising a sub-antibiotic dose of azithromycin, further comprising a dicarboxylic acid (e.g., azelaic acid).

The methods described herein might be useful for treating both anterior blepharitis and posterior blepharitis simultaneously. In some embodiments, anterior blepharitis and posterior blepharitis are treated by administration of a single pharmaceutical formulation. In certain embodiments, anterior blepharitis and posterior blepharitis are treated with alternating administration of a first pharmaceutical formulation and a second pharmaceutical formulation. In some embodiments, the dicarboxylic acid (e.g., azelaic acid) addresses anterior blepharitis and the sub-antibiotic dose of azithromycin addresses posterior blepharitis. In certain embodiments, the dicarboxylic acid (e.g., azelaic acid) and the sub-antiparasitic dose of azithromycin are part of a single formulation. In certain embodiments, the dicarboxylic acid (e.g., azelaic acid) and the sub-antibiotic dose of an azithromycin are separate formulations.

Alternatively, the antiparasitic applied in a sub-antiparasitic dose to treat blepharitis may be an avermectin. In some embodiments, provided herein is a method for treating blepharitis in a subject in need thereof, comprising administering to the subject a pharmaceutical formulation comprising a sub-antiparasitic dose of an avermectin. In some embodiments, provided herein is a method for treating blepharitis in a subject in need thereof, comprising administering to the subject a pharmaceutical formulation comprising a sub-antiparasitic dose of an avermectin, wherein; (a) the pharmaceutical formulation is administered to the eyelid, and (b) the pharmaceutical formulation is administered daily for at least 1 month. Methods of treating blepharitis in a subject in need thereof may comprise administering a pharmaceutical formulation comprising a sub-antiparasitic dose of an avermectin, further comprising a dicarboxylic acid (e.g., azelaic acid). In some embodiments, the avermectin is ivermectin.

The methods described herein might be useful for treating both anterior blepharitis and posterior blepharitis simultaneously. In some embodiments, anterior blepharitis and posterior blepharitis are treated by administration of a single pharmaceutical formulation. In certain embodiments, anterior blepharitis and posterior blepharitis are treated with alternating administration of a first pharmaceutical formulation and a second pharmaceutical formulation. In some embodiments, the dicarboxylic acid (e.g., azelaic acid) addresses anterior blepharitis and the sub-antiparasitic dose of an antiparasitic addresses posterior blepharitis. In certain embodiments, the dicarboxylic acid (e.g., azelaic acid) and the sub-antiparasitic dose of an antiparasitic are part of a single formulation. In certain embodiments, the dicarboxylic acid (e.g., azelaic acid) and the sub-antiparasitic dose of an antiparasitic are separate formulations.

As described above, blepharitis might describe several sub-conditions. In some embodiments, the blepharitis is anterior blepharitis. In some embodiments, the blepharitis is posterior blepharitis. In some embodiments, the blepharitis is anterior and posterior blepharitis.

Generally, the methods described herein might be useful for increasing secretion of meibum. The increase of meibum may, for instance, result from the disclosed formulations improving meibum amount or quality by altering the lipid chemistry, lowering the meibum melting temperature, or liquefying hardened meibum. In some embodiments, provided herein is a method for increasing secretion of meibum in a subject in need thereof. In some embodiments, provided herein is a method for increasing secretion of meibum in a subject in need thereof, comprising administering to the subject a pharmaceutical formulation comprising a sub-antibiotic dose of an antibiotic. In some embodiments, provided herein is a method for increasing secretion of meibum in a subject in need thereof, comprising administering to the subject a pharmaceutical formulation comprising a sub-antibiotic dose of an antibiotic, wherein; (a) the pharmaceutical formulation is administered to the eyelid, and (b) the pharmaceutical formulation is administered daily for at least 1 month. Methods for increasing secretion of meibum in a subject in need thereof may comprise administering a pharmaceutical formulation comprising a sub-antibiotic dose of an antibiotic, further comprising a dicarboxylic acid (e.g., azelaic acid). In certain embodiments, meibum fluidity is increased. In some embodiments, meibum melting temperature is lowered.

In some embodiments, provided herein is a method for increasing secretion of meibum in a subject in need thereof, comprising administering to the subject a pharmaceutical formulation comprising a sub-antiparasitic dose of an antiparasitic. In some embodiments, provided herein is a method for increasing secretion of meibum in a subject in need thereof, comprising administering to the subject a pharmaceutical formulation comprising a sub-antiparasitic dose of an antiparasitic, wherein; (a) the pharmaceutical formulation is administered to the eyelid, and (b) the pharmaceutical formulation is administered daily for at least 1 month. Methods for increasing secretion of meibum in a subject in need thereof may comprise administering a sub-antiparasitic dose of an antiparasitic, further comprising a dicarboxylic acid (e.g., azelaic acid).

In some embodiments, provided herein is a method for increasing secretion of meibum in a subject in need thereof, comprising administering to the subject a pharmaceutical formulation comprising a dicarboxylic acid (e.g., azelaic acid). In some embodiments, provided herein is a method for increasing secretion of meibum in a subject in need thereof, comprising administering to the subject a pharmaceutical formulation comprising a dicarboxylic acid (e.g., azelaic acid), wherein; (a) the pharmaceutical formulation is administered to the eyelid, and (b) the pharmaceutical formulation is administered daily for at least 1 month.

Methods for increasing secretion of meibum described herein may benefit from alternating administration of a two or more pharmaceutical formulations described herein. Thus, in some embodiments, a method for increasing secretion of meibum in a subject in need thereof, comprises alternating administration of a first pharmaceutical formulation and a second pharmaceutical formulation to the eyelids. In some embodiments, the first pharmaceutical formulation comprises a sub-antibiotic dose of azithromycin and is applied daily and the second pharmaceutical formulation comprises a sub-antiparasitic dose of an avermectin and is applied daily. In some embodiments, the first pharmaceutical formulation comprises a sub-antibiotic dose of azithromycin and is applied daily and the second pharmaceutical formulation comprises a sub-antiparasitic dose of a dicarboxylic acid (e.g., azelaic acid) and is applied daily. In some embodiments, the first pharmaceutical formulation comprises a sub-antiparasitic dose of ivermectin and is applied daily and the second pharmaceutical formulation comprises a sub-antiparasitic dose of a dicarboxylic acid (e.g., azelaic acid) and is applied daily. Administration of the two pharmaceutical formulations may be alternated daily, weekly, monthly, or every 2, 3, 4, 5, 6, 7, 8, 9, 10, 11, or 12 months.

In some embodiments, the alternating administration comprises alternating the first and second pharmaceutical formulations daily. In some embodiments, the alternating administration comprises alternating the first and second pharmaceutical formulations monthly. In some embodiments, the alternating administration comprises alternating the first and second pharmaceutical formulations every two months.

In some embodiments, the antibiotic applied in a sub-antibiotic dose to increase secretion of meibum may be azithromycin. In some embodiments, provided herein is a method for increasing secretion of meibum in a subject in need thereof. In some embodiments, provided herein is a method for increasing secretion of meibum in a subject in need thereof, comprising administering to the subject a pharmaceutical formulation comprising a sub-antibiotic dose of azithromycin. In some embodiments, provided herein is a method for increasing secretion of meibum in a subject in need thereof, comprising administering to the subject a pharmaceutical formulation comprising a sub-antibiotic dose of azithromycin, wherein; (a) the pharmaceutical formulation is administered to the eyelid, and (b) the pharmaceutical formulation is administered daily for at least 1 month. Methods for increasing secretion of meibum in a subject in need thereof may comprise administering a pharmaceutical formulation comprising a sub-antibiotic dose of an azithromycin, further comprising a dicarboxylic acid (e.g., azelaic acid).

Alternatively, the antiparasitic applied in a sub-antiparasitic dose to increase production of meibum may be an avermectin. In some embodiments, provided herein is a method for increasing secretion of meibum in a subject in need thereof, comprising administering to the subject a pharmaceutical formulation comprising a sub-antiparasitic dose of an avermectin. In some embodiments, provided herein is a method for increasing secretion of meibum in a subject in need thereof, comprising administering to the subject a pharmaceutical formulation comprising a sub-antiparasitic dose of an avermectin, wherein; (a) the pharmaceutical formulation is administered to the eyelid, and (b) the pharmaceutical formulation is administered daily for at least 1 month. Methods for increasing secretion of meibum in a subject in need thereof may comprise administering a pharmaceutical formulation comprising a sub-antiparasitic dose of an avermectin, further comprising a dicarboxylic acid (e.g., azelaic acid). In some embodiments, the avermectin is ivermectin.

The mechanisms of action of the formulations and methods described herein, as discussed above, are premised upon different mechanisms of action than are typically intended with use of the chemical agents (i.e., to treat bacterial or parasitic infection, to treat inflammation). Subjects who would benefit from the disclosed formulations and methods might not have a bacterial infection of the eye. In some embodiments, the subject in need thereof does not have a parasitic infection of the eye. In some embodiments, the subject in need thereof does not have a bacterial infection of the eye and does not have a parasitic infection of the eye. In some embodiments, the subject in need thereof does not have a clinically diagnosable parasitic infection of the eye. In some embodiments, the subject in need thereof does not have a clinically diagnosable parasitic infection of the eye. In this context, "clinically diagnosable" means the parasitic or bacterial infection results in symptoms of infection, and is differentiated from asymptomatic surface colonization.

Because the pharmaceutical formulations described herein increase the quality or quantity of meibum, they may be useful in enhancing the safety or efficacy of existing treatments (e.g., expression, at-home hot compresses, in-office energy-based devices), or addressing the deficiencies thereof. In some embodiments, provided herein is a method of enhancing the safety and efficacy of currently available DED treatments. In some embodiments, provided herein is a method of enhancing the safety and efficacy of currently available MGD treatments. In some embodiments, the pharmaceutical formulations described herein may be used prior to using existing treatments for dry eye disease. In some embodiments, provided herein are methods of using existing treatments (e.g., heat-based therapies) in combination with the methods and formulations described herein. For example, existing treatments may be used before, concurrently with, or after any of the methods disclosed herein.

The pharmaceutical formulations of any of the methods described herein may be administered to the eyelid. In some embodiments, the pharmaceutical formulation is administered directly to the outer (e.g., external) surface of the eyelid (e.g., external skin of the eyelid, above the lid margin, above the upper lashes, below the lower lashes). In some embodiments, the pharmaceutical formulation is administered to the skin of the eyelid and not to the eyelid margin. In certain embodiments, the formulation may penetrate the skin of the eyelid and be delivered to one or more meibomian glands. In certain embodiments, the pharmaceutical formulation is administered directly to the eyelid margin. In certain embodiments, the pharmaceutical formulation is administered to the eyelid indirectly. In certain embodiments, the pharmaceutical formulation is administered to the eyelid indirectly, having been applied to the ocular surface, making contact with the inner surface of the eyelid. In certain embodiments, the pharmaceutical formulation is administered to the eyelid indirectly, having been applied to the ocular surface, making contact with the eyelid margin. In some embodiments, the pharmaceutical formulation is administered to the eyelid via an ocular insert.

Application of the pharmaceutical formulation of the methods disclosed herein could be achieved via administration by any route suitable for delivery to the eye. For instance, it may be useful to apply the pharmaceutical formulation via a dropper. In some embodiments, the formulation may be applied via an applicator stick. In some embodiments, the formulation may be applied by the finger. In some embodiments, the formulation may be applied via an ocular insert. In some embodiments, the pharmaceutical formulation may be rolled on or sprayed on.

As described above, the methods and formulations described herein may be suitable for treating one or more condition of the eye, wherein improvement is observed in one or more symptoms of the condition of the eye. This improvement may be quantified in a number of ways. For instance, the methods and formulations described herein may result in reduced matrix metalloproteinase (e.g., MMP 9) activity in tears or secretions. In some embodiments, matrix metalloproteinase activity may decrease by at least 5%, 10%, 20%, 30%, 40%, 50%, 60%, 70%, or 80%). In certain embodiments, the methods and formulations described herein may result in more liquified meibum, as quantified by an increased meibomian gland secretion score. In some embodiments, the meibomian gland secretion score may increase by at least 5%, 10%, 20%, 30%, 40%, 50%, 60%, 70%, 80%, 90%, 100%, 200%, 300%, or 400%. In certain embodiments, the methods and formulations described herein may result in increased lipid layer thickness, as measured by, for example, lipid layer interferometry. In some embodiments, the lipid layer thickness may increase by at least 5%, 10%, 20%, 30%, 40%, 50%, 60%, 70%, 80%, 90%, 100%, or 200%. In certain embodiments, the methods and formulations described herein may result in increased tear breakup times (TBUT). In some embodiments, TBUT may increase by at least 5%, 10%, 20%, 30%, 40%, 50%, 60%, 70%, 80%, 90%, 100%, 200%, 300%, or 400%. In certain embodiments, the methods and formulations described herein may result in fewer symptoms reported by patients in subjective questionnaires (e.g., Standard Patient Evaluation of Eye Dryness (SPEED); Ocular Surface Disease Index (OSDI), Symptom Assessment Questionnaire in Dry Eye (SANDE)). For instance, the methods and formulations may reduce SPEED symptoms, reduce OSDI symptoms, reduce SANDE symptoms, and/or reduce Eye Dryness Score symptoms. In some embodiments, symptoms may be reduced by at least 5%, 10%, 20%, 30%, 40%, or 50%. In certain embodiments, the methods and formulations described herein may result in reduced injury to the ocular surface, as evaluated by corneal and conjunctival staining. For instance, the methods and formulations described herein may result in decreased corneal and/or conjunctival staining. In some embodiments, staining may decrease by at least 5%, 10%, 20%, 30%, 40%, 50%, 60%, 70%, 80%, 90%, or 100%. In certain embodiments, the methods and formulations described herein may result in a decrease in the number of obstructed, capped, and/or keratinized meibomian glands. In some embodiments, the number of obstructed, capped, and/or keratinized meibomian glands may decrease by at least 5%, 10%, 20%, 30%, 40%, 50%, 60%, 70%, 80%, 90%, or 100%. In some embodiments, the methods and formulations described herein may result in reduced tear osmolarity. In some embodiments, tear osmolarity may be reduced by at least 5%, 10%, 20%, 30%, 40%, or 50%. In some embodiments, the methods and formulations described herein may result in reduced demodex mite counts.

The methods and formulations described herein may result in vision enhancement. In some embodiments, the methods and formulations described herein may result in contact lens wear improvement (e.g., less wear). In certain embodiments, the methods and formulations described herein may result in reading speed enhancement. In some embodiments, the methods and formulations described herein may improve cataract surgery outcomes by improving the accuracy of pre-op measurements due to an improvement in tear film quality.

In some embodiments of the methods and formulations described herein, an improvement may be observed in one or more of the aforementioned symptoms of the condition of the eye as measured over the course of, or after, between about 1 week and about 1 year or greater after beginning application of a formulation. In some embodiments, the improvement may be observed after 1, 2, 3, 4, 5, 6, 7, 8, 9, 10, 11, or 12 weeks. In certain embodiments, the improvement may be observed after 1, 2, 3, 4, 5, 6, 7, 8, 9, 10, 11, 12, 13, 14, 15, 16, 17, 18, 19, 20, 21, 22, 23, or 24 months. In some embodiments, the improvement may be observed between 1 and 24, between 1 and 18, between 1 and 12, between 1 and 6, between 1 and 2, between 2 and 4, between 2 and 6, between 2 and 12, between 2 and 18, between 2 and 24, between 3 and 24, between 3 and 18, between 3 and 12, between 6 and 24, between 6 and 18, between 6 and 12, between 12 and 24, between 12 and 18, or between 18 and 24 months.

Kits

In some embodiments, this disclosure also provides a pharmaceutical package or kit comprising one or more containers filled with at least one pharmaceutical formulation of this disclosure. Optionally associated with such a contains(s) can be an applicator for the formulation. The applicator could, for instance, be a dropper, applicator stick, or ocular insert. Further associated with such a container(s) can optionally be a notice in the form prescribed by a governmental agency regulating the manufacture, use or sale of pharmaceuticals or biological products, which notice reflects (a) approval by the agency of manufacture, use or sale for human administration, (b) directions for use, or both. Instructions for use may also be provided.

In some embodiments, a pharmaceutical package or kit may include a heat therapy device (e.g., TearCare®).

The foregoing applies to any of the pharmaceutical formulations, methods, and uses described herein. This disclosure specifically contemplates any combination of the features of such pharmaceutical formulations, methods, and uses (alone or in combination) with the features described for the various kits described in this section.

Although methods and materials similar or equivalent to those described herein can be used in the practice or testing of the present disclosure, illustrative methods and materials are described herein. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs.

Each embodiment described herein may be taken alone or in combination with any one or more other embodiments.

Exemplary Embodiments

Embodiment I-1. A method for treating dry eye disease in a subject in need thereof, comprising administering to the subject a pharmaceutical formulation comprising a sub-antibiotic dose of azithromycin, wherein
a) the pharmaceutical formulation is administered to the eyelid, and
b) the pharmaceutical formulation is administered daily for at least 1 month.

Embodiment I-2. A method for treating blepharitis in a subject in need thereof, comprising administering to the subject a pharmaceutical formulation comprising a sub-antibiotic dose of azithromycin, wherein
a) the pharmaceutical formulation is administered to the eyelid, and
b) the pharmaceutical formulation is administered daily for at least 1 month.

Embodiment I-3. A method for increasing secretion of meibum in a subject in need thereof, comprising administering to the subject a pharmaceutical formulation comprising a sub-antibiotic dose of azithromycin, wherein
a) the pharmaceutical formulation is administered to the eyelid, and
b) the pharmaceutical formulation is administered daily for at least 1 month.

Embodiment I-4. A method for treating dry eye disease in a subject in need thereof, comprising administering to the subject a pharmaceutical formulation comprising a sub-antiparasitic dose of an avermectin, wherein
a) the pharmaceutical formulation is administered to the eyelid, and
b) the pharmaceutical formulation is administered daily for at least 1 month.

Embodiment I-5. A method for treating blepharitis in a subject in need thereof, comprising administering to the subject a pharmaceutical formulation comprising a sub-antiparasitic dose of an avermectin, wherein
 a) the pharmaceutical formulation is administered to the eyelid, and
 b) the pharmaceutical formulation is administered daily for at least 1 month.

Embodiment I-6. A method for increasing secretion of meibum in a subject in need thereof, comprising administering to the subject a pharmaceutical formulation comprising a sub-antiparasitic dose of an avermectin, wherein
 a) the pharmaceutical formulation is administered to the eyelid, and
 b) the pharmaceutical formulation is administered daily for at least 1 month.

Embodiment I-7. The method of any one of embodiments I-4 to I-6, wherein the avermectin is ivermectin.

Embodiment I-8. The method of any one of embodiments I-1 to I-7, wherein the subject in need thereof does not have a bacterial infection of the eye.

Embodiment I-9. The method of any one of embodiments I-1 to I-7, wherein the subject in need thereof does not have a parasitic infection of the eye.

Embodiment I-10. The method of any one of embodiments I-1 to I-3 or I-8 to I-9, wherein the pharmaceutical formulation further comprises an avermectin.

Embodiment I-11. The method of any one of embodiments I-4 to I-10, wherein the pharmaceutical formulation further comprises azithromycin.

Embodiment I-12. The method of any one of embodiments I-1 to I-11 wherein the pharmaceutical formulation further comprises at least one skin penetration enhancer.

Embodiment I-13. The method of any one of embodiments I-1 to I-12, wherein the pharmaceutical formulation further comprises an immunosuppressant.

Embodiment I-14. The method of embodiment 1-13, wherein the immunosuppressant is selected from the group consisting of cyclosporine, tacrolimus, and lifitegrast.

Embodiment I-15. The method of any one of embodiments I-1 to I-3, I-8 to I-10, or I-12 to I-14, wherein the pharmaceutical formulation comprises less than 1% w/v azithromycin.

Embodiment I-16. The method of any one of embodiments I-1 to I-3, I-8 to I-10, or I-12 to I-14, wherein the pharmaceutical formulation comprises 0.5% w/v or less azithromycin.

Embodiment I-17. The method of any one of embodiments I-1 to I-3, I-8 to I-10, or I-12 to I-14, wherein the pharmaceutical formulation comprises 0.1% w/v or less azithromycin.

Embodiment I-18. The method of any one of embodiments I-1 to I-3, I-8 to I-10, or I-12 to I-14, wherein the pharmaceutical formulation comprises 0.01% w/v or less azithromycin.

Embodiment I-19. The method of any one of embodiments I-4 to I-9 or I-11 to I-14, wherein the pharmaceutical formulation comprises less than 1% w/v of an avermectin.

Embodiment I-20. The method of any one of embodiments I-4 to I-9 or I-11 to I-14, wherein the pharmaceutical formulation comprises 0.5% w/v or less of an avermectin.

Embodiment I-21. The method of any one of embodiments I-4 to I-9 or I-11 to I-14, wherein the pharmaceutical formulation comprises 0.1% w/v or less of an avermectin.

Embodiment I-22. The method of any one of embodiments I-4 to I-9 or I-11 to I-14, wherein the pharmaceutical formulation comprises 0.01% w/v or less of an avermectin.

Embodiment I-23. The method of any one of embodiments I-1 to I-22, wherein the pharmaceutical formulation is administered daily for 2 months.

Embodiment I-24. The method of any one of embodiments I-1 to I-22, wherein the pharmaceutical formulation is administered daily for 6 months.

Embodiment I-25. The method of any one of embodiments I-1 to I-10, wherein the pharmaceutical formulation is applied daily for at least 1 year.

Embodiment I-26. The method of any one of embodiments I-1 to I-25, wherein the pharmaceutical formulation is applied as a cream, gel suspension, solution, ointment, or spray.

Embodiment I-27. The method of any one of embodiments I-1 to I-25, wherein the pharmaceutical formulation is applied as drops.

Embodiment I-28. A pharmaceutical formulation for treating a condition of the eye, comprising a sub-antibiotic dose of azithromycin.

Embodiment I-29. A pharmaceutical formulation for treating a condition of the eye, comprising a sub-antiparasitic dose of an avermectin.

Embodiment I-30. A pharmaceutical formulation for treating a condition of the eye, comprising a sub-antibiotic dose of azithromycin and a sub-antiparasitic dose of an avermectin.

Embodiment I-31. A pharmaceutical formulation for treating a condition of the eye, comprising a sub-antibiotic dose of azithromycin or a sub-antiparasitic dose of an avermectin, and further comprising an immunosuppressant.

Embodiment II-1. A method for treating dry eye disease in a subject in need thereof, comprising administering to the subject a pharmaceutical formulation comprising a sub-antibiotic dose of azithromycin, wherein
 a) the pharmaceutical formulation is administered to the eyelid, and
 b) the pharmaceutical formulation is administered daily for at least 1 month.

Embodiment II-2. A method for treating blepharitis in a subject in need thereof, comprising administering to the subject a pharmaceutical formulation comprising a sub-antibiotic dose of azithromycin, wherein
 a) the pharmaceutical formulation is administered to the eyelid, and
 b) the pharmaceutical formulation is administered daily for at least 1 month.

Embodiment II-3. A method for increasing secretion of meibum in a subject in need thereof, comprising administering to the subject a pharmaceutical formulation comprising a sub-antibiotic dose of azithromycin, wherein
 a) the pharmaceutical formulation is administered to the eyelid, and
 b) the pharmaceutical formulation is administered daily for at least 1 month.

Embodiment II-4. A method for treating dry eye disease in a subject in need thereof, comprising administering to the subject a pharmaceutical formulation comprising a sub-antiparasitic dose of an avermectin, wherein
 a) the pharmaceutical formulation is administered to the eyelid, and
 b) the pharmaceutical formulation is administered daily for at least 1 month.

Embodiment II-5. A method for treating blepharitis in a subject in need thereof, comprising administering to the subject a pharmaceutical formulation comprising a sub-antiparasitic dose of an avermectin, wherein a) the pharmaceutical formulation is administered to the eyelid, and b) the pharmaceutical formulation is administered daily for at least 1 month.

Embodiment II-6. A method for increasing secretion of meibum in a subject in need thereof, comprising administering to the subject a pharmaceutical formulation comprising a sub-antiparasitic dose of an avermectin, wherein a) the pharmaceutical formulation is administered to the eyelid, and b) the pharmaceutical formulation is administered daily for at least 1 month.

Embodiment II-7. The method of any one of embodiments II-4 to II-6, wherein the avermectin is ivermectin.

Embodiment II-8. The method of any one of embodiments II-1 to II-7, wherein the subject in need thereof does not have a bacterial infection of the eye.

Embodiment II-9. The method of any one of embodiments II-1 to II-7, wherein the subject in need thereof does not have a parasitic infection of the eye.

Embodiment II-10. The method of any one of embodiments II-1 to II-3 or II-8 to II-9, wherein the pharmaceutical formulation further comprises an avermectin.

Embodiment II-11. The method of any one of embodiments II-4 to II-10, wherein the pharmaceutical formulation further comprises azithromycin.

Embodiment II-12. The method of any one of embodiments II-1 to II-11 wherein the pharmaceutical formulation further comprises at least one skin penetration enhancer.

Embodiment II-13. The method of any one of embodiments II-1 to II-12, wherein the pharmaceutical formulation further comprises an immunosuppressant.

Embodiment II-14. The method of embodiment II-13, wherein the immunosuppressant is selected from the group consisting of cyclosporine, tacrolimus, and lifitegrast.

Embodiment II-15. The method of any one of embodiments II-1 to II-3, II-8 to II-10, or II-12 to II-14, wherein the pharmaceutical formulation comprises less than 1% w/v azithromycin.

Embodiment II-16. The method of any one of embodiments II-1 to II-3, II-8 to II-10, or II-12 to II-14, wherein the pharmaceutical formulation comprises 0.5% w/v or less azithromycin.

Embodiment II-17. The method of any one of embodiments II-1 to II-3, II-8 to II-10, or II-12 to II-14, wherein the pharmaceutical formulation comprises 0.1% w/v or less azithromycin.

Embodiment II-18. The method of any one of embodiments II-1 to II-3, II-8 to II-10, or II-12 to II-14, wherein the pharmaceutical formulation comprises 0.01% w/v or less azithromycin.

Embodiment II-19. The method of any one of embodiments II-4 to II-9 or II-11 to II-14, wherein the pharmaceutical formulation comprises less than 1% w/v of an avermectin.

Embodiment II-20. The method of any one of embodiments II-4 to II-9 or II-11 to II-14, wherein the pharmaceutical formulation comprises 0.5% w/v or less of an avermectin.

Embodiment II-21. The method of any one of embodiments II-4 to II-9 or II-11 to II-14, wherein the pharmaceutical formulation comprises 0.1% w/v or less of an avermectin.

Embodiment II-22. The method of any one of embodiments II-4 to II-9 or II-11 to II-14, wherein the pharmaceutical formulation comprises 0.01% w/v or less of an avermectin.

Embodiment II-23. The method of any one of embodiments II-1 to II-22, wherein the pharmaceutical formulation is administered daily for 2 months.

Embodiment II-24. The method of any one of embodiments II-1 to II-22, wherein the pharmaceutical formulation is administered daily for 6 months.

Embodiment II-25. The method of any one of embodiments II-1 to II-10, wherein the pharmaceutical formulation is applied daily for at least 1 year.

Embodiment II-26. The method of any one of embodiments II-1 to II-25, wherein the pharmaceutical formulation is applied as a cream, gel, suspension, solution, ointment, or spray.

Embodiment II-27. The method of any one of embodiments II-1 to II-25, wherein the pharmaceutical formulation is applied as drops.

Embodiment II-28. The method of any one of embodiments II-1 to II-27, wherein the pharmaceutical formulation further comprises azelaic acid.

Embodiment II-29. The method of embodiment II-28, wherein the concentration of azelaic acid is between about 1% and about 20%.

Embodiment II-30. The method of embodiments II-28 to II-29, wherein the concentration of azelaic acid is between about 10% and about 15%.

Embodiment II-31. The method of any one of embodiments II-28 to II-30, wherein the pharmaceutical formulation comprises between about 10% and about 20% azelaic acid and about 0.4% to about 0.5% azithromycin.

Embodiment II-32. The method of any one of embodiments II-1 to II-31 further comprising at least one of mineral oil, petrolatum, propylene glycol, and polyethylene glycol.

Embodiment II-33. A method for treating dry eye disease in a subject in need thereof, comprising alternating administration of a first pharmaceutical formulation and a second pharmaceutical formulation to the eyelid, wherein a) the first pharmaceutical formulation comprises a sub-antibiotic dose of azithromycin and is applied daily, and b) the second pharmaceutical formulation comprises a sub-antiparasitic dose of an avermectin and is applied daily.

Embodiment II-34. A method for treating blepharitis in a subject in need thereof, comprising alternating administration of a first pharmaceutical formulation and a second pharmaceutical formulation to the eyelid, wherein a) the first pharmaceutical formulation comprises a sub-antibiotic dose of azithromycin and is applied daily, and b) the second pharmaceutical formulation comprises a sub-antiparasitic dose of an avermectin and is applied daily.

Embodiment II-35. A method for increasing secretion of meibum in a subject in need thereof, comprising alternating administration of a first pharmaceutical formulation and a second pharmaceutical formulation to the eyelids, wherein a) the first pharmaceutical formulation comprises a sub-antibiotic dose of azithromycin and is applied daily, and b) the second pharmaceutical formulation comprises a sub-antiparasitic dose of an avermectin and is applied daily.

Embodiment II-36. The method of any one of embodiments II-33 to II-35, wherein the alternating administration comprises alternating the first and second pharmaceutical formulations daily.

Embodiment II-37. The method of any one of embodiments II-33 to II-35, wherein the alternating administration comprises alternating the first and second pharmaceutical formulations monthly.

Embodiment II-38. The method of any one of embodiments II-33 to II-35, wherein the alternating administration comprises alternating the first and second pharmaceutical formulation every two months.

Embodiment II-39. The method of any one of embodiments II-33 to II-38, wherein the avermectin is ivermectin.

Embodiment II-40. The method of any one of embodiments II-33 to II-39, wherein the subject in need thereof does not have a bacterial infection of the eye.

Embodiment II-41. The method of any one of embodiments II-33 to II-40, wherein the subject in need thereof does not have a parasitic infection of the eye.

Embodiment II-42. The method of any one of embodiments II-33 to II-41, wherein the pharmaceutical formulation further comprises at least one skin penetration enhancer.

Embodiment II-43. The method of any one of embodiments II-33 to II-42, wherein the pharmaceutical formulation further comprises an immunosuppressant.

Embodiment II-44. The method of embodiment II-43 wherein the immunosuppressant is selected from the group consisting of cyclosporine, tacrolimus, and lifitegrast.

Embodiment II-45. The method of any one of embodiments II-33 to II-44, wherein the first pharmaceutical formulation comprises less than 1% w/v azithromycin.

Embodiment II-46. The method of any one of embodiments II-33 to II-45, wherein the first pharmaceutical formulation comprises 0.5% w/v or less azithromycin.

Embodiment II-47. The method of any one of embodiments II-33 to II-46, wherein the first pharmaceutical formulation comprises 0.1% w/v or less azithromycin.

Embodiment II-48. The method of any one of embodiments II-33 to II-47, wherein the first pharmaceutical formulation comprises 0.01% w/v or less azithromycin.

Embodiment II-49. The method of any one of embodiments II-33 to II-48, wherein the second pharmaceutical formulation comprises less than 1% w/v of an avermectin.

Embodiment II-50. The method of any one of embodiments II-33 to II-49, wherein the second pharmaceutical formulation comprises 0.5% w/v or less of an avermectin.

Embodiment II-51. The method of any one of embodiments II-33 to II-50, wherein the second pharmaceutical formulation comprises 0.1% w/v or less of an avermectin.

Embodiment II-52. The method of any one of embodiments II-33 to II-51, wherein the second pharmaceutical formulation comprises 0.01% w/v or less of an avermectin.

Embodiment II-53. The method of any one of embodiments II-33 to II-52, wherein each of the first pharmaceutical formulation and the second pharmaceutical formulations is applied as one of a cream, gel, suspension, solution, ointment, or spray.

Embodiment II-54. The method of any one of embodiments II-33 to II-52, wherein the first pharmaceutical formulation and the second pharmaceutical formulation are applied as drops.

Embodiment II-55. A method of treating dry eye disease or blepharitis in a subject in need thereof, comprising administering to the subject a pharmaceutical formulation comprising azelaic acid, wherein:

a) the pharmaceutical formulation is administered to the eyelid, and b) the pharmaceutical formulation is administered daily for at least 1 month.

Embodiment II-56. A method of treating blepharitis in a subject in need thereof, comprising administering to the subject a pharmaceutical formulation comprising azelaic acid, wherein:

a) the pharmaceutical formulation is administered to the eyelid, and b) the pharmaceutical formulation is administered daily for at least 1 month.

Embodiment II-57. A method of increasing secretion of meibum in a subject in need thereof, comprising administering to the subject a pharmaceutical formulation comprising azelaic acid, wherein:

a) the pharmaceutical formulation is administered to the eyelid, and b) the pharmaceutical formulation is administered daily for at least 1 month.

Embodiment II-58. The method of any one of embodiments II-55 to II-57, wherein the pharmaceutical formulation is administered once daily.

Embodiment II-59. The method of any one of embodiments II-55 to II-57, wherein the pharmaceutical formulation is administered twice daily.

Embodiment II-60. The method of any one of embodiments II-55 to II-59, wherein the concentration of azelaic acid is between about 1% and about 20%.

Embodiment II-61. The method of any one of embodiments II-55 to II-60, wherein the concentration of azelaic acid is between about 10% and about 15%.

Embodiment II-62. The method of any one of embodiments II-55 to II-61 wherein the pharmaceutical formulation further comprises at least one skin penetration enhancer.

Embodiment II-63. The method of any one of embodiments II-55 to II-62, wherein the pharmaceutical formulation is administered daily for at least 2 months.

Embodiment II-64. The method of any one of embodiments II-55 to II-63, wherein the pharmaceutical formulation is administered daily for at least 6 months.

Embodiment II-65. The method of any one of embodiments II-55 to II-64, wherein the pharmaceutical formulation is administered daily for at least 1 year.

Embodiment II-66. The method of any one of embodiments II-55 to II-65, wherein the pharmaceutical formulation is applied as a cream, gel, suspension, solution, ointment, or spray.

Embodiment II-67. The method of any one of embodiments II-55 to II-65, wherein the pharmaceutical formulation is applied as drops.

Embodiment II-68. A pharmaceutical formulation for treating a condition of the eye, comprising a sub-antibiotic dose of azithromycin.

Embodiment II-69. A pharmaceutical formulation for treating a condition of the eye, comprising a sub-antiparasitic dose of an avermectin.

Embodiment II-70. A pharmaceutical formulation for treating a condition of the eye, comprising a sub-antibiotic dose of azithromycin and a sub-antiparasitic dose of an avermectin.

Embodiment II-71. A pharmaceutical formulation for treating a condition of the eye, comprising a sub-antibiotic dose of azithromycin or a sub-antiparasitic dose of an avermectin, and further comprising an immunosuppressant.

Embodiment II-72. A pharmaceutical formulation for treating a condition of the eye, comprising a sub-antibiotic dose of azithromycin or a sub-antiparasitic dose of an avermectin, and further comprising azelaic acid.

Embodiment II-73. The pharmaceutical formulation of embodiment II-72, comprising between about 0.4% and 0.5% azithromycin and between about 10% and 15% azelaic acid.

Embodiment II-74. A pharmaceutical formulation for treating a condition of the eye, comprising azelaic acid.

Embodiment II-75. The pharmaceutical formulation of embodiment II-74 comprising between about 10% and 15% azelaic acid.

Embodiment II-76. A method for treating dry eye disease, treating blepharitis, or increasing secretion of meibum in a subject in need thereof, comprising administering to the eyelid of the subject a pharmaceutical formulation comprising:
 a) between about 5% and about 15% azelaic acid, and
 b) between about 0.4% to about 0.5% azithromycin;
 wherein, the pharmaceutical formulation is administered daily for at least 1 month.

Embodiment II-77. The method of any one of embodiment II-2, 11-5, II-34, II-55 or II-76, wherein the blepharitis is caused by demodex mites.

Embodiment II-78. The method of embodiment II-76, wherein the azelaic acid addresses anterior blepharitis and the azithromycin addresses posterior blepharitis.

Embodiment II-79. The pharmaceutical formulation of embodiment II-74 or II-75, wherein the azelaic acid addresses anterior blepharitis.

Embodiment II-80. A method for treating a condition of the eye comprising administering to the subject a pharmaceutical formulation comprising:
 a) a sub-antibiotic dose of azithromycin;
 b) a sub-antiparasitic dose of an avermectin;
 c) a sub-antibiotic dose of azithromycin and a sub-antiparasitic dose of an avermectin;
 d) a sub-antibiotic dose of azithromycin or a sub-antiparasitic dose of an avermectin, and further comprising an immunosuppressant;
 e) a sub-antibiotic dose of azithromycin or a sub-antiparasitic dose of an avermectin, and further comprising azelaic acid; or
 f) azelaic acid;
 wherein the pharmaceutical formulation is applied to the eyelid daily for at least 1 month.

Embodiment II-81. The method of embodiment II-80, wherein the condition of the eye is one or more of dry eye disease, blepharitis, and meibomian gland dysfunction.

Embodiment II-82. The pharmaceutical formulation of any one of embodiments II-68 to II-75, wherein the condition of the eye is one or more of dry eye disease, blepharitis, and meibomian gland dysfunction.

Embodiment III-1. A method for treating dry eye disease in a subject in need thereof, comprising administering to the subject a pharmaceutical formulation comprising a sub-antibiotic dose of azithromycin, wherein
 a) the pharmaceutical formulation is administered to the eyelid, and
 b) the pharmaceutical formulation is administered daily for at least 1 month.

Embodiment III-2. A method for treating blepharitis in a subject in need thereof, comprising administering to the subject a pharmaceutical formulation comprising a sub-antibiotic dose of azithromycin, wherein
 a) the pharmaceutical formulation is administered to the eyelid, and
 b) the pharmaceutical formulation is administered daily for at least 1 month.

Embodiment III-3. A method for increasing secretion of meibum in a subject in need thereof, comprising administering to the subject a pharmaceutical formulation comprising a sub-antibiotic dose of azithromycin, wherein
 a) the pharmaceutical formulation is administered to the eyelid, and
 b) the pharmaceutical formulation is administered daily for at least 1 month.

Embodiment III-4. A method for treating dry eye disease in a subject in need thereof, comprising administering to the subject a pharmaceutical formulation comprising a sub-antiparasitic dose of an avermectin, wherein
 a) the pharmaceutical formulation is administered to the eyelid, and
 b) the pharmaceutical formulation is administered daily for at least 1 month.

Embodiment III-5. A method for treating blepharitis in a subject in need thereof, comprising administering to the subject a pharmaceutical formulation comprising a sub-antiparasitic dose of an avermectin, wherein
 a) the pharmaceutical formulation is administered to the eyelid, and
 b) the pharmaceutical formulation is administered daily for at least 1 month.

Embodiment III-6. A method for increasing secretion of meibum in a subject in need thereof, comprising administering to the subject a pharmaceutical formulation comprising a sub-antiparasitic dose of an avermectin, wherein
 a) the pharmaceutical formulation is administered to the eyelid, and
 b) the pharmaceutical formulation is administered daily for at least 1 month.

Embodiment III-7. The method of any one of embodiments III-4 to III-6, wherein the avermectin is ivermectin.

Embodiment III-8. The method of any one of embodiments III-1 to III-7, wherein the subject in need thereof does not have a bacterial infection of the eye.

Embodiment III-9. The method of any one of embodiments III-1 to III-7, wherein the subject in need thereof does not have a parasitic infection of the eye.

Embodiment III-10. The method of any one of embodiments III-1 to III-3 or III-8 to III-9, wherein the pharmaceutical formulation further comprises an avermectin.

Embodiment III-11. The method of any one of embodiments III-4 to III-10, wherein the pharmaceutical formulation further comprises azithromycin.

Embodiment III-12. The method of any one of embodiments III-1 to III-11 wherein the pharmaceutical formulation further comprises at least one skin penetration enhancer.

Embodiment III-13. The method of any one of embodiments III-1 to III-12, wherein the pharmaceutical formulation further comprises an immunosuppressant.

Embodiment III-14. The method of embodiment III-13, wherein the immunosuppressant is selected from the group consisting of cyclosporine, tacrolimus, and lifitegrast.

Embodiment III-15. The method of any one of embodiments III-1 to III-3, III-8 to III-10, or III-12 to III-14, wherein the pharmaceutical formulation comprises less than 1% w/v azithromycin.

Embodiment III-16. The method of any one of embodiments III-1 to III-3, III-8 to III-10, or III-12 to III-14, wherein the pharmaceutical formulation comprises 0.5% w/v or less azithromycin.

Embodiment III-17. The method of any one of embodiments III-1 to III-3, III-8 to III-10, or III-12 to III-14, wherein the pharmaceutical formulation comprises 0.1% w/v or less azithromycin.

Embodiment III-18. The method of any one of embodiments III-1 to III-3, III-8 to III-10, or III-12 to III-14, wherein the pharmaceutical formulation comprises 0.01% w/v or less azithromycin.

Embodiment III-19. The method of any one of embodiments III-4 to III-9 or III-11 to III-14, wherein the pharmaceutical formulation comprises less than 1% w/v of an avermectin.

Embodiment III-20. The method of any one of embodiments III-4 to III-9 or III-11 to III-14, wherein the pharmaceutical formulation comprises 0.5% w/v or less of an avermectin.

Embodiment III-21. The method of any one of embodiments III-4 to III-9 or III-11 to III-14, wherein the pharmaceutical formulation comprises 0.1% w/v or less of an avermectin.

Embodiment III-22. The method of any one of embodiments III-4 to III-9 or III-11 to III-14, wherein the pharmaceutical formulation comprises 0.01% w/v or less of an avermectin.

Embodiment III-23. The method of any one of embodiments III-1 to III-22, wherein the pharmaceutical formulation is administered daily for 2 months.

Embodiment III-24. The method of any one of embodiments III-1 to III-22, wherein the pharmaceutical formulation is administered daily for 6 months.

Embodiment III-25. The method of any one of embodiments III-1 to III-10, wherein the pharmaceutical formulation is administered daily for at least 1 year.

Embodiment III-26. The method of any one of embodiments III-1 to III-25, wherein the pharmaceutical formulation is administered as a cream, gel, suspension, solution, ointment, or spray.

Embodiment III-27. The method of any one of embodiments III-1 to III-25, wherein the pharmaceutical formulation is administered as drops.

Embodiment III-28. The method of any one of embodiments III-1 to III-27, wherein the pharmaceutical formulation further comprises azelaic acid.

Embodiment III-29. The method of embodiment III-28, wherein the concentration of azelaic acid is between about 1% and about 20%.

Embodiment III-30. The method of embodiments III-28 to III-29, wherein the concentration of azelaic acid is between about 10% and about 15%.

Embodiment III-31. The method of any one of embodiments III-28 to III-30, wherein the pharmaceutical formulation comprises between about 10% and about 20% azelaic acid and about 0.4% to about 0.5% azithromycin.

Embodiment III-32. The method of any one of embodiments III-1 to III-31 further comprising at least one of mineral oil, petrolatum, propylene glycol, and polyethylene glycol.

Embodiment III-33. A method for treating dry eye disease in a subject in need thereof, comprising alternating administration of a first pharmaceutical formulation and a second pharmaceutical formulation to the eyelid, wherein a) the first pharmaceutical formulation comprises a sub-antibiotic dose of azithromycin and is administered daily, and b) the second pharmaceutical formulation comprises a sub-antiparasitic dose of an avermectin and is administered daily.

Embodiment III-34. A method for treating blepharitis in a subject in need thereof, comprising alternating administration of a first pharmaceutical formulation and a second pharmaceutical formulation to the eyelid, wherein a) the first pharmaceutical formulation comprises a sub-antibiotic dose of azithromycin and is administered daily, and b) the second pharmaceutical formulation comprises a sub-antiparasitic dose of an avermectin and is administered daily.

Embodiment III-35. A method for increasing secretion of meibum in a subject in need thereof, comprising alternating administration of a first pharmaceutical formulation and a second pharmaceutical formulation to the eyelids, wherein a) the first pharmaceutical formulation comprises a sub-antibiotic dose of azithromycin and is administered daily, and b) the second pharmaceutical formulation comprises a sub-antiparasitic dose of an avermectin and is administered daily.

Embodiment III-36. The method of any one of embodiments III-33 to III-35, wherein the alternating administration comprises alternating the first and second pharmaceutical formulations daily.

Embodiment III-37. The method of any one of embodiments III-33 to III-35, wherein the alternating administration comprises alternating the first and second pharmaceutical formulations monthly.

Embodiment III-38. The method of any one of embodiments III-33 to III-35, wherein the alternating administration comprises alternating the first and second pharmaceutical formulation every two months.

Embodiment III-39. The method of any one of embodiments III-33 to III-38, wherein the avermectin is ivermectin.

Embodiment III-40. The method of any one of embodiments III-33 to III-39, wherein the subject in need thereof does not have a bacterial infection of the eye.

Embodiment III-41. The method of any one of embodiments III-33 to III-40, wherein the subject in need thereof does not have a parasitic infection of the eye.

Embodiment III-42. The method of any one of embodiments III-33 to III-41, wherein the pharmaceutical formulation further comprises at least one skin penetration enhancer.

Embodiment III-43. The method of any one of embodiments III-33 to III-42, wherein the pharmaceutical formulation further comprises an immunosuppressant.

Embodiment III-44. The method of embodiment III-43 wherein the immunosuppressant is selected from the group consisting of cyclosporine, tacrolimus, and lifitegrast.

Embodiment III-45. The method of any one of embodiments III-33 to III-44, wherein the first pharmaceutical formulation comprises less than 1% w/v azithromycin.

Embodiment III-46. The method of any one of embodiments III-33 to III-45, wherein the first pharmaceutical formulation comprises 0.5% w/v or less azithromycin.

Embodiment III-47. The method of any one of embodiments III-33 to III-46, wherein the first pharmaceutical formulation comprises 0.1% w/v or less azithromycin.

Embodiment III-48. The method of any one of embodiments III-33 to III-47, wherein the first pharmaceutical formulation comprises 0.01% w/v or less azithromycin.

Embodiment III-49. The method of any one of embodiments III-33 to III-48, wherein the second pharmaceutical formulation comprises less than 1% w/v of an avermectin.

Embodiment III-50. The method of any one of embodiments III-33 to III-49, wherein the second pharmaceutical formulation comprises 0.5% w/v or less of an avermectin.

Embodiment III-51. The method of any one of embodiments III-33 to III-50, wherein the second pharmaceutical formulation comprises 0.1% w/v or less of an avermectin.

Embodiment III-52. The method of any one of embodiments III-33 to III-51, wherein the second pharmaceutical formulation comprises 0.01% w/v or less of an avermectin.

Embodiment III-53. The method of any one of embodiments III-33 to III-52, wherein each of the first pharmaceutical formulation and the second pharmaceutical formulations is administered as one of a cream, gel, suspension, solution, ointment, or spray.

Embodiment III-54. The method of any one of embodiments III-33 to III-52, wherein the first pharmaceutical formulation and the second pharmaceutical formulation are administered as drops.

Embodiment III-55. A method of treating dry eye disease in a subject in need thereof, comprising administering to the subject a pharmaceutical formulation comprising azelaic acid, wherein:
a) the pharmaceutical formulation is administered to the eyelid, and
b) the pharmaceutical formulation is administered daily for at least 1 month.

Embodiment III-56. A method of treating blepharitis in a subject in need thereof, comprising administering to the subject a pharmaceutical formulation comprising azelaic acid, wherein:
a) the pharmaceutical formulation is administered to the eyelid, and
b) the pharmaceutical formulation is administered daily for at least 1 month.

Embodiment III-57. A method of increasing secretion of meibum in a subject in need thereof, comprising administering to the subject a pharmaceutical formulation comprising azelaic acid, wherein:
a) the pharmaceutical formulation is administered to the eyelid, and
b) the pharmaceutical formulation is administered daily for at least 1 month.

Embodiment III-58. The method of any one of embodiments III-55 to III-57, wherein the pharmaceutical formulation is administered once daily.

Embodiment III-59. The method of any one of embodiments III-55 to III-57, wherein the pharmaceutical formulation is administered twice daily.

Embodiment III-60. The method of any one of embodiments III-55 to III-59, wherein the concentration of azelaic acid is between about 1% and about 20%.

Embodiment III-61. The method of any one of embodiments III-55 to III-60, wherein the concentration of azelaic acid is between about 10% and about 15%.

Embodiment III-62. The method of any one of embodiments III-55 to III-61 wherein the pharmaceutical formulation further comprises at least one skin penetration enhancer.

Embodiment III-63. The method of any one of embodiments III-55 to III-62, wherein the pharmaceutical formulation is administered daily for at least 2 months.

Embodiment III-64. The method of any one of embodiments III-55 to III-63, wherein the pharmaceutical formulation is administered daily for at least 6 months.

Embodiment III-65. The method of any one of embodiments III-55 to III-64, wherein the pharmaceutical formulation is administered daily for at least 1 year.

Embodiment III-66. The method of any one of embodiments III-55 to III-65, wherein the pharmaceutical formulation is administered as a cream, gel, suspension, solution, ointment, or spray.

Embodiment III-67. The method of any one of embodiments III-55 to III-65, wherein the pharmaceutical formulation is administered as drops.

Embodiment III-68. A pharmaceutical formulation for treating a condition of the eye, comprising a sub-antibiotic dose of azithromycin.

Embodiment III-69. A pharmaceutical formulation for treating a condition of the eye, comprising a sub-antiparasitic dose of an avermectin.

Embodiment III-70. A pharmaceutical formulation for treating a condition of the eye, comprising a sub-antibiotic dose of azithromycin and a sub-antiparasitic dose of an avermectin.

Embodiment III-71. A pharmaceutical formulation for treating a condition of the eye, comprising a sub-antibiotic dose of azithromycin or a sub-antiparasitic dose of an avermectin, and further comprising an immunosuppressant.

Embodiment III-72. A pharmaceutical formulation for treating a condition of the eye, comprising a sub-antibiotic dose of azithromycin or a sub-antiparasitic dose of an avermectin, and further comprising azelaic acid.

Embodiment III-73. The pharmaceutical formulation of embodiment III-72, comprising between about 0.4% and 0.5% azithromycin and between about 10% and 15% azelaic acid.

Embodiment III-74. A pharmaceutical formulation for treating a condition of the eye, comprising azelaic acid.

Embodiment III-75. The pharmaceutical formulation of embodiment III-74 comprising between about 10% and 15% azelaic acid.

Embodiment III-76. A method for treating dry eye disease, treating blepharitis, or increasing secretion of meibum in a subject in need thereof, comprising administering to the eyelid of the subject a pharmaceutical formulation comprising:
a) between about 5% and about 15% azelaic acid, and
b) between about 0.4% to about 0.5% azithromycin;
wherein, the pharmaceutical formulation is administered daily for at least 1 month.

Embodiment III-77. The method of any one of embodiments III-2, III-5, III-34, III-55 or III-76, wherein the blepharitis is caused by demodex mites.

Embodiment III-78. The method of embodiment III-76, wherein the azelaic acid addresses anterior blepharitis and the azithromycin addresses posterior blepharitis.

Embodiment III-79. The pharmaceutical formulation of embodiment III-74 or III-75, wherein the azelaic acid addresses anterior blepharitis.

Embodiment III-80. A method for treating a condition of the eye comprising administering to the subject a pharmaceutical formulation comprising:
a) a sub-antibiotic dose of azithromycin;
b) a sub-antiparasitic dose of an avermectin;
c) a sub-antibiotic dose of azithromycin and a sub-antiparasitic dose of an avermectin;
d) a sub-antibiotic dose of azithromycin or a sub-antiparasitic dose of an avermectin, and further comprising an immunosuppressant;
e) a sub-antibiotic dose of azithromycin or a sub-antiparasitic dose of an avermectin, and further comprising azelaic acid; or
f) azelaic acid;
wherein the pharmaceutical formulation is administered to the eyelid daily for at least 1 month.

Embodiment III-81. The method of embodiment III-80, wherein the condition of the eye is one or more of dry eye disease, blepharitis, and meibomian gland dysfunction.

Embodiment III-82. The pharmaceutical formulation of any one of embodiments III-68 to III-75, wherein the condition of the eye is one or more of dry eye disease, blepharitis, and meibomian gland dysfunction.

Embodiment III-83. A method of treating dry eye disease comprising administering to an external surface of an eyelid of a subject a pharmaceutical formulation comprising azelaic acid, wherein the administration of said pharmaceutical formulation reduces a symptom of dry eye disease.

Embodiment III-84. The method of embodiment III-83, wherein the dry eye disease is tear deficient dry eye.

Embodiment III-85. The method of embodiment III-83, wherein the dry eye disease is evaporative dry eye.

Embodiment III-86. The method of embodiment III-83, wherein the symptom of dry eye disease is meibomian gland dysfunction, redness, stinging, burning, itching, light sensitivity, watery eyes, blurry vision, irregularities of the ocular surface, or damage to corneal or conjunctival epithelium and tissues.

Embodiment III-87. The method of embodiment III-83, wherein the administration of said pharmaceutical formulation further improves the amount or quality of meibum produced.

Embodiment III-88. The method of embodiment III-83, wherein the dry eye disease does not result from infection or inflammation of tissue.

Embodiment III-89. The method of embodiments III-83, wherein the pharmaceutical formulation is administered daily.

Embodiment III-90. The method of embodiment III-83, wherein the pharmaceutical formulation is administered twice daily.

Embodiment III-91. The method of embodiment III-83, wherein the pharmaceutical formulation is administered daily for at least 6 months.

Embodiment III-92. The method of embodiment III-83, wherein the pharmaceutical formulation is administered daily for at least 1 year.

Embodiment III-93. The method of embodiment III-83, wherein the pharmaceutical formulation is administered as a cream, gel, suspension, solution, ointment, or spray.

Embodiment III-94. The method of embodiment III-93, wherein the pharmaceutical formulation is administered as a cream.

Embodiment III-95. The method of embodiment III-93, wherein the pharmaceutical formulation is administered as a gel.

Embodiment III-96. The method of embodiment III-83, wherein a concentration of azelaic acid in the pharmaceutical formulation is between about 1% and about 20%.

Embodiment III-97. The method of embodiment III-96, wherein the concentration of azelaic acid in the pharmaceutical formulation is between about 10% and about 15%.

Embodiment III-98. The method of embodiment III-83, wherein the pharmaceutical formulation further comprises azithromycin.

Embodiment III-99. The method of embodiment III-98, wherein a concentration of azithromycin in the pharmaceutical formulation is between about 0.1% and 0.5%.

Embodiment III-100. The method of embodiment III-83, wherein the pharmaceutical formulation further comprises an avermectin.

Embodiment III-101. The method of embodiment III-98, wherein a concentration of the avermectin in the pharmaceutical formulation is between about 0.1% and 0.5%.

Embodiment III-102. The method of embodiment III-100, wherein the avermectin is ivermectin.

Embodiment III-103. The method of embodiment III-83, wherein the pharmaceutical formulation further comprises at least one skin penetration enhancer.

Embodiment III-104. A method of treating blepharitis comprising administering to an external surface of an eyelid of a subject a pharmaceutical formulation comprising azelaic acid, wherein the administration of said pharmaceutical formulation reduces a symptom of blepharitis.

Embodiment III-105. The method of embodiment III-104, wherein the blepharitis is anterior blepharitis.

Embodiment III-106. The method of embodiment III-104, wherein the blepharitis is posterior blepharitis.

Embodiment III-107. The method of embodiment III-104, wherein the symptom of blepharitis is irritation, reddening, itching, burning, edema, or crusting.

Embodiment III-108. The method of embodiment III-104, wherein the administration of said pharmaceutical formulation further improves the amount or quality of meibum produced.

Embodiment III-109. The method of embodiment III-104, wherein the blepharitis does not result from bacterial or parasitic infection.

Embodiment III-110. The method of embodiment III-104, wherein the pharmaceutical formulation is administered daily.

Embodiment III-111. The method of embodiment III-104, wherein the pharmaceutical formulation is administered twice daily.

Embodiment III-112. The method of embodiment III-110, wherein the pharmaceutical formulation is administered daily for at least 6 months.

Embodiment III-113. The method of embodiment III-110, wherein the pharmaceutical formulation is administered daily for at least 1 year.

Embodiment III-114. The method of embodiment III-104, wherein the pharmaceutical formulation is administered as a cream, gel, suspension, solution, ointment, or spray.

Embodiment III-115. The method of embodiment III-114, wherein the pharmaceutical formulation is administered as a cream.

Embodiment III-116. The method of embodiment III-114, wherein the pharmaceutical formulation is administered as a gel.

Embodiment III-117. The method of embodiment III-104, wherein a concentration of azelaic acid in the pharmaceutical formulation is between about 1% and about 20%.

Embodiment III-118. The method of embodiment III-117, wherein the concentration of azelaic acid in the pharmaceutical formulation is between about 10% and about 15%.

Embodiment III-119. The method of embodiment III-104, wherein the pharmaceutical formulation further comprises azithromycin.

Embodiment III-120. The method of embodiment III-119, wherein a concentration of azithromycin in the pharmaceutical formulation is between about 0.1% and 0.5%.

Embodiment III-121. The method of embodiment III-104, wherein the pharmaceutical formulation further comprises an avermectin.

Embodiment III-122. The method of embodiment III-121, wherein a concentration of the avermectin in the pharmaceutical formulation is between about 0.1% and 0.5%.

Embodiment III-123. The method of embodiment III-104, wherein the pharmaceutical formulation further comprises at least one skin penetration enhancer.

Embodiment III-124. A method for increasing secretion of meibum comprising administering to an external surface of an eyelid of a subject a pharmaceutical formulation comprising azelaic acid, wherein the administration of said pharmaceutical formulation reduces a symptom of inadequate tear production or poor quality of tears.

Embodiment III-125. The method of embodiment III-124, wherein meibum fluidity is increased.

Embodiment III-126. The method of embodiment III-124, wherein meibum melting temperature is lowered.

Embodiment III-126B. The method of embodiment III-124, wherein the symptom of inadequate tear production or poor quality of tears is excessive evaporation of water from the ocular surface.

Embodiment III-127. The method of embodiment III-124, wherein the symptom of inadequate tear production or poor quality of tears is redness, stinging, burning, itching, light sensitivity, watery eyes, blurry vision, irregularities of the ocular surface, or damage to corneal or conjunctival epithelium and tissues.

Embodiment III-128. The method of embodiment III-124, wherein the pharmaceutical formulation is administered daily.

Embodiment III-129. The method of embodiment III-124, wherein the pharmaceutical formulation is administered twice daily.

Embodiment III-130. The method of embodiment III-128, wherein the pharmaceutical formulation is administered daily for at least 6 months.

Embodiment III-131. The method of embodiment III-128, wherein the pharmaceutical formulation is administered daily for at least 1 year.

Embodiment III-132. The method of embodiment III-124, wherein the pharmaceutical formulation is administered as a cream, gel, suspension, solution, ointment, or spray.

Embodiment III-133. The method of embodiment III-132, wherein the pharmaceutical formulation is administered as a cream.

Embodiment III-134. The method of embodiment III-132, wherein the pharmaceutical formulation is administered as a gel.

Embodiment III-135. The method of embodiment III-124, wherein a concentration of azelaic acid in the pharmaceutical formulation is between about 1% and about 20%.

Embodiment III-136. The method of embodiment III-135, wherein the concentration of azelaic acid in the pharmaceutical formulation is between about 10% and about 15%.

Embodiment III-137. The method of embodiment III-124, wherein the pharmaceutical formulation further comprises azithromycin.

Embodiment III-138. The method of embodiment III-137, wherein a concentration of azithromycin in the pharmaceutical formulation is between about 0.1% and 0.5%.

Embodiment III-139. The method of embodiment III-124, wherein the pharmaceutical formulation further comprises an avermectin.

Embodiment III-140. A method for treating dry eye disease, comprising administering to an external surface of an eyelid of a subject a pharmaceutical formulation comprising:
 a) between about 1% and about 20% azelaic acid; and
 b) between about 0.1% and about 0.5% azithromycin,
wherein the pharmaceutical formulation is administered to the external surface of the eyelid daily for at least 1 month, and wherein administering the pharmaceutical formulation reduces a symptom of dry eye disease.

Embodiment III-141. The method of embodiment III-140, wherein the symptom of dry eye disease is meibomian gland dysfunction, redness, stinging, burning, itching, light sensitivity, watery eyes, blurry vision, irregularities of the ocular surface, or damage to corneal or conjunctival epithelium and tissues.

Embodiment III-142. The method of embodiment III-140, wherein the dry eye disease is aqueous tear-deficient dry eye (ADDE).

Embodiment III-143. The method of embodiment III-140, wherein the dry eye disease is evaporative dry eye (EDE).

Embodiment III-144. The method of embodiment III-140, wherein ADDE and EDE are treated simultaneously.

Embodiment III-145. The method of embodiment III-140, wherein the administration of said pharmaceutical formulation further reduces a symptom of blepharitis.

Embodiment III-146. The method of embodiment III-145, wherein the blepharitis is anterior blepharitis.

Embodiment III-147. The method of embodiment III-145, wherein the blepharitis is posterior blepharitis.

Embodiment III-148. The method of embodiment III-145, wherein the blepharitis is both anterior blepharitis and posterior blepharitis.

Embodiment III-149. The method of embodiment III-140, wherein the administration of said pharmaceutical formulation further improves the amount or quality of meibum produced.

Embodiment III-150. The method of embodiment III-140, wherein the dry eye disease does not result from bacterial infection, parasitic infection, or inflammation of tissue.

Embodiment III-151. The method of embodiment III-140, wherein the concentration of azelaic acid is between about 5% and 20%.

Embodiment III-152. The method of embodiment III-140, wherein the concentration of azelaic acid is between about 5% and 15%.

Embodiment III-153. The method of embodiment III-140, wherein the concentration of azelaic acid is between about 5% and 15% and the concentration of azithromycin is between about 0.4% and about 0.5%.

Embodiment III-154. The method of embodiment III-140, wherein the concentration of azelaic acid is about 10% and the concentration of azithromycin is about 0.4%.

Embodiment III-155. The method of embodiment III-140, wherein the pharmaceutical formulation is administered twice daily.

Embodiment III-156. The method of embodiment III-140, wherein the pharmaceutical formulation is administered daily for at least 6 months.

Embodiment III-157. The method of embodiment III-140, wherein the pharmaceutical formulation is administered daily for at least 1 year.

Embodiment III-158. The method of embodiment III-140, wherein the pharmaceutical formulation is administered as a cream, gel, suspension, solution, ointment, or spray.

Embodiment III-159. The method of embodiment III-157, wherein the pharmaceutical formulation is administered as a cream.

Embodiment III-160. The method of embodiment III-157, wherein the pharmaceutical formulation is administered as a gel.

Embodiment III-161. The method of embodiment III-162, wherein the pharmaceutical formulation further comprises at least one skin penetration enhancer.

Embodiment III-162. The method of any one of embodiments III-1 to III-32, III-55 to III-67, III-76 to III-161, wherein the pharmaceutical formulation further comprises at least one polyol.

Embodiment III-163. The method of any one of embodiments III-33 to III-54, wherein the first pharmaceutical formulation and the second pharmaceutical formulation each independently comprise at least one polyol.

Embodiment III-164. The pharmaceutical formulation of any one of embodiments III-68 to III-75, wherein the pharmaceutical formulation further comprises at least one polyol.

Embodiment III-165. The method of embodiment III-162 or III-163, wherein the at least one polyol is selected from propylene glycol, polyethylene glycol, glycerol, erythritol, mannitol, or sorbitol.

Embodiment III-166. The method of embodiment III-165, wherein the at least one polyol is propylene glycol.

Embodiment III-167. A pharmaceutical formulation comprising between about 1% and about 20% azelaic acid and between about 0.1% and about 0.5% azithromycin.

Embodiment III-168. Use of the pharmaceutical formulation of any one of embodiments 111-68 to III-75, or III-167 in the manufacture of a medicament for treating a condition of the eye or for increasing secretion of meibum.

Embodiment III-169. Use of the pharmaceutical formulation of any one of embodiments 111-68 to III-75, or III-167 as a medicament for treating a condition of the eye or for increasing secretion of meibum.

Embodiment III-170. Use of the pharmaceutical formulation of any one of embodiments 111-68 to III-75, or III-167 for treating a condition of the eye or for increasing secretion of meibum.

Embodiment III-171. The use of any one of embodiments III-168 to III-170 wherein the condition of the eye is dry eye disease or blepharitis.

EXAMPLES

Example 1: Human Clinical Trials for Pharmaceutical Formulations

Human subjects diagnosed with dry eye disease are assigned to arms for treatment with one of four formulations: (1) azithromycin, (2) azelaic acid, (3) azithromycin and azelaic acid, or (4) vehicle only. Each patient is given a baseline exam of visual acuity, intraocular pressure, slit lamp exam, conjunctival and corneal staining, meibomian gland scoring, tear break up time, SPEED questionnaire, and subjective dry eye questionnaires (SANDE).

Subjects are treated by nightly or twice daily with administration of the respective formulation for at least one month. Subjects are examined at 1 week, 2 weeks, and 4 weeks. Trial endpoints are based on tear break up time, meibomian gland scores, corneal and conjunctival staining (decreased is good, increased may indicate toxicity), and questionnaires. Toxicity is detected by increased staining of cornea or conjunctiva. Patients may be assessed by one or more of matrix metalloproteinase activity, meibomian gland secretion scoring, lipid layer interferometry, tear break up time, subjective questionnaires (SPEED, OSDI, SANDE), corneal and conjunctival staining, meibomian gland obstructions, or tear osmolarity.

What is claimed is:

1. A method for treating dry eye disease comprising:
administering a pharmaceutical formulation comprising between about 1% and about 20% azelaic acid,
wherein the pharmaceutical formulation is administered to an external surface of the lower eyelid below lower lashes daily for at least 1 month, and wherein administering the pharmaceutical formulation reduces a symptom of dry eye disease.

2. The method of claim 1, wherein the symptom of dry eye disease is meibomian gland dysfunction, redness, stinging, burning, itching, light sensitivity, watery eyes, blurry vision, irregularities of the ocular surface, damage to corneal or conjunctival epithelium and tissues, or combinations thereof.

3. The method of claim 1, wherein the administration results in one or more of: an increased tear break up time, an increase in meibomian gland secretion score, a decrease in corneal staining, and a decrease in conjunctival staining.

4. The method of claim 1, wherein the dry eye disease is aqueous tear-deficient dry eye (ADDE).

5. The method of claim 1, wherein the dry eye disease is evaporative dry eye (EDE).

6. The method of claim 1, wherein the dry eye disease is aqueous tear-deficient dye eye(ADDE) and evaporative dry eye(EDE), and wherein the ADDE and EDE are treated simultaneously.

7. The method of claim 1, wherein the administration of said pharmaceutical formulation reduces a symptom of blepharitis.

8. The method of claim 1, wherein the administration of said pharmaceutical formulation further improves the amount or quality of meibum produced.

9. The method of claim 1, wherein the dry eye disease does not result from bacterial infection, parasitic infection, or inflammation of tissue.

10. The method of claim 1, wherein the concentration of azelaic acid is between about 2% and about 6%.

11. The method of claim 1, wherein the concentration of azelaic acid is between about 2% and about 6%.

12. The method of claim 1, wherein the concentration of azelaic acid is about 3%.

13. The method of claim 1, wherein the concentration of azelaic acid is about 4%.

14. The method of claim 1, wherein the pharmaceutical formulation further comprises azithromycin.

15. The method of claim 14, wherein the concentration of azithromycin is between about 0.1% and about 1%.

16. The method of claim 14, wherein the concentration of azithromycin is about 0.5%.

17. The method of claim 1, wherein the pharmaceutical formulation is administered once daily for at least 1 month.

18. The method of claim 1, wherein the pharmaceutical formulation is administered once or twice daily for at least 6 months.

19. The method of claim 1, wherein the pharmaceutical formulation is administered once or twice daily for at least 1 year.

20. The method of claim 1, wherein the pharmaceutical formulation is administered as a cream, gel, suspension, solution, ointment, or spray.

21. The method of claim 1, wherein the pharmaceutical formulation further comprises at least one skin penetration enhancer.

22. The method of claim 1, wherein the pharmaceutical formulation further comprises at least one polyol.

23. The method of claim 22, wherein the at least one polyol is propylene glycol, polyethylene glycol, glycerol, erythritol, mannitol, or sorbitol.

24. The method of claim 23, wherein the at least one polyol is propylene glycol.

25. A method for treating dry eye disease comprising:
administering a pharmaceutical formulation comprising between about 1% and about 20% azelaic acid,
wherein the pharmaceutical formulation is administered to an external surface of the lower eyelid below a lower lid margin daily for at least 1 month, and wherein administering the pharmaceutical formulation reduces a symptom of a dry eye disease.

26. The method of claim 25, wherein the pharmaceutical formulation comprises between about 2% and about 6% azelaic acid.

27. The method of claim 25, wherein the pharmaceutical formulation further comprises between about 0.1% and about 1% azithromycin.

* * * * *